United States Patent [19]

O'Hara

[11] Patent Number: 5,874,264
[45] Date of Patent: Feb. 23, 1999

[54] GIBBON APE LEUKEMIA VIRUS RECEPTOR

[75] Inventor: Bryan Mark O'Hara, Pearl River, N.Y.

[73] Assignee: American Cyanamid Company, Madison, N.J.

[21] Appl. No.: 436,900

[22] Filed: May 8, 1995

Related U.S. Application Data

[60] Division of Ser. No. 674,287, Mar. 25, 1991, Pat. No. 5,414,076, which is a continuation-in-part of Ser. No. 398,351, Aug. 24, 1989, abandoned.

[51] Int. Cl.$^6$ .......................... C07K 18/705; C12N 15/10; C12N 15/12
[52] U.S. Cl. .......................... 435/172.3; 435/6; 435/69.1; 435/320.1; 530/350; 530/23.5
[58] Field of Search .................................. 435/6, 7.1, 7.2, 435/252.3, 32.1, 372.3; 514/2; 530/350; 536/23.5

[56] References Cited

PUBLICATIONS

O'Hara, Bryan M. et al., Cell Growth & Differentiation, 119–127 (1990).

*Primary Examiner*—John Ulm
*Attorney, Agent, or Firm*—Elizabeth M. Barnhard; Karen A. Lowney

[57] ABSTRACT

The present invention relates to novel purified gibbon ape leukemia receptor proteins and purified DNA sequences encoding these receptor proteins.

4 Claims, 18 Drawing Sheets

```
  1 GAGCTGTCCCCGGTGCCGCCGGGCCCGGACCCGGTGCCGGTGCTGCCGTGCTC     50
 51 CAGCCGCTGCCCTGCGATCTCCTCCGTCTCCGCTCCGCCCCTCCCTTTC        100
101 CCTGGATGAACTTGGTCCTTCTCTCTCCGCCATGGAATTCTGCTCCG          150
151 TGCTTTTAGCCCTCCTGAGCCAAGAAACCCAGACAACAGATGCCCATA         200
201 CGCAGCGTATAGCAGTAACTCCCCAGCTCGGTTTCTGTGCCGTAGTTTAC       250
251 AGTATTAATTTTATATATATATATTATTATAGCATTTTTGATAC             300
301 CTCATATTCTGTTTACACATCTTGAAAGGCGCTCAGTAGTTCTTCTACTA       350
351 AACAACCACTACTCCAGAGAATGGCAACGCTGATTACCAGTACACAGCT        400
401 GCTACCGCCGCTTCTGGTCCTTTGGTGGACTACCTATGGATGCTCATCCT       450
451 GGGCTTCATTATTGCATTTGTCTTGGCATTCTCCGTGGGAGCCAATGATG       500
501 TAGCAAATTCTTTTGGTACAGCTGTGGGCTCAGTGTAGTGACCCTGAAG        550
551 CAAGCCTGCATCCTAGCTAGCATCTTTGAAACAGTGGGCTCTGTCTTACT       600
601 GGGGCCAAAGTGAGCGAAACCATCCGGAAGGGCTTGATTGACGTGGAGA        650
651 TGTACAACTCGACTCAAGGGCTACTGATGGCCGGCTCAGTCAGTGCTATG       700
701 TTTGGTTCTGCTGTGTGGCCAACTCGTGGCTTCGTTTTTGAAGCTCCCTAT      750
751 TTCTGAACCCATTGTATTGTTGGTGCAACTATTGGTTTCTCCCTCGTGG        800
801 CAAAGGGCAGGAGGGTGTCAAGTGTCTGAACTGGTCTGAATAAAATTGTGATG    850
851 TCTTGGTTCGTGTCCCACTGCTTTCTGCTGGAATTAGTCTGGAATTTATT       900
901 CTTCCTGGTTCGTTCGTGCATTCATCCTCCATAAGGCAGATCCAGTTCCTAATG   950
951 GTTTGCGAGCTTTGCCAGTTTTCTATGCCTGCACAGTTGGAATAAACCTC      1000
```

FIG. 6A

```
1001  TTTCCATCATGTATACTGGAGCACCGTTGCTGGCTTTGACAAACTTCC  1050
      ----,----+----,----+----,----+----,----+----,----+
1051  TCTGTGGGTACCATCCTCATCTCGGTGGGATGTGCAGTTTCTGTGCCC  1100
1101  TTATCGTCTGGTTCTTTGTATGTCCCAGGATGAAGAGAAAATTGAACGA  1150
1151  GAAATAAAGTGTAGTCCTTCTGAAGCCCCTTAATGGAAAAAAGAATAG  1200
1201  CTTGAAAGAAGACCATGAAGAACAAAGTTGTCTGTTGGTGATATTGAAA  1250
      ----,----+----,----+----,----+----,----+----,----+
1251  ACAAGCATCCTGTTTCTGAGGTAGGGCCTGCCACTGTGCCCCTCCAGGCT  1300
1301  GTGGTGGAGGAGAGAACAGTCTCATTCAAACTTGGAGATTGGAGGAAGC  1350
1351  TCCAGAGAGAGAGAGGCTTCCCAGCTGGACTTGAAAGAGGAAACCAGCA  1400
1401  TAGATAGCACCGTGAATGGTGCAGTTGCAGTTGCCTAATGGGAACCTTGTC  1450
1451  CAGTTCAGTCAAGCCGTCAGCAACCAAATAAACTCCAGTGGCCACTCCCA  1500
      ----,----+----,----+----,----+----,----+----,----+
1501  GTATCACACCGTGCATAAGGATTCCGGCCTGTACAAAGAGCTACTCCATA  1550
1551  AATTACATCTTGCCAAGTGGTGGGAGATTGGGAGACTCCGGTGACAAA  1600
1601  CCCTTAAGGCGCAATAATAGCTATACTTCCTATACCATGGCAATATGTGG  1650
1651  CATGCCTCTCGATTCATTCCGTGCCAAAGAAGGTGAACAGAAGGGCGAAG  1700
1701  AAATGGAGAAGCTGACAGCTAAGCCCTAATGCAGAGTCAGACTCCAAGAAGCGAATTCGA  1750
      ----,----+----,----+----,----+----,----+----,----+
1751  ATGGACAGTTACACCAGTTACTGCCAATGCTGTGTCTCTGACCTTCACTCAGC  1800
1801  ATCTGAGATAGACATGAGTGCTTCAAGGCAGCGATGGGTCTAGGTGACAGAA  1850
1851  AAGGAAGTAATGCCTCTCCAGAAGAATGCTATGACCAGGATAAGCCTGAA  1900
1901  GTCTCTCCTCCTTCAGTTCCTGCAGATCCTTACAGCCTGCTTTGGTC  1950
1951  ATTCGCCCATGGTGGCAATGACGTAAGCAATGCCATTGGGCCTCTGGTTG  2000
      ----,----+----,----+----,----+----,----+----,----+
2001  CTTTATATATTTGGTTTATGACACAGGAGATGTTTCTTCAAAAGTGGCAACA  2050
2051  CCAATATGGCTTCTACTCTATGTGGTGTTTGGTATCTGTGTTGGTCTGTG  2100
2101  GGTTTGGGAAGAAGAGTTATCCAGAACCATGGGAAGGATCTGACACCGA  2150
2151  TCACCCCTCTAGTGGCTTCAGTATTGAACTGGCATCTGCCCCTCACTGTG  2200
2201  GTGATTGCATCAAATATTGGCCTTCCCATCAGTACAACACATTGTAAAGT  2250
```

FIG.6B

```
2251 GGGCTCTGTGTGTCTGTTGCTGCTGGCTCCGGTCCAAGAAGGCTGTTGACT 2300
2301 GGCGTCTCTTCGTAACATTTTATGGCCTGGTTTGTCACAGTCCCCATT 2350
2351 TCTGGAGTTATCAGTGCTGCTGCCATCATGGCAATCTTCAGATATGTCATCCT 2400
2401 CAGAATGTGAAGCTGTTTGAGATTAAAATTTGTGTCAATGTTTGGGACCA 2450
2451 TCTTAGGTATTCCCTGCTCCCCCTGAAGAATGATTACAGTGTTAACAGAAGA 2500
2501 CTGACAAGAGTCTTTTTATTTGGGAGCAGAGAGGAAGTGTTACTTGTG 2550
2551 CTATAACTGCTTTTGTGCTAAATATGAATTGTCTCAAAATTAGCTGTGTA 2600
2601 AAATAGCCCGGGTTCCACTGGCTCCCTGCTGAGGTCCCCTTTCCTTCTGGG 2650
2651 CTGTGAATTCCTGTACATATTCTCTACTTTTTGTATCAGGCTTCAATTC 2700
2701 CATTATGTTTTAATGTTGTCTCTGAAGATGACTTGTGATTTTTTTTCTT 2750
2751 TTTTTAAACCATGAAGAGCCGTTTGACAGAGCATGCTCTGCGTTGTTGG 2800
2801 TTTCACCAGCTTCTGCCCTCACATGCACAGGATTAACAACAAAAATAT 2850
2851 AACTACAACTTCCCTGTAGTCTCTTATATAAGAGTCCTTGGTACTC 2900
2901 TGCCCTCCCTGTCAGTAGTGGCAGGATCTATTGGCATATTCGGGAGCTTCT 2950
2951 TAGAGGGATGAGGTTCTTTGAACACAGTGAAAATTTAAATTAGTAACTTT 3000
3001 TTTGCAAGCAGTTTATTGACTGTTATTGCTAAGAAGTAAGAAAGAAA 3050
3051 AAGCCTGTTGGCAATCTGTTATTCTTTAAGATTTCTGGCAGTGTGG 3100
3101 ATGGATGAATGAAGTGGAATGTGAACTTTGGGCAAGTAAATGGGACAGC 3150
3151 CTTCCATGTTCATTTGTCTACCCTCTTAACTGAATAAAAAGCCTACAGTT 3200
3201 TTTAGAAAAAA 3220
```

FIG.6C

| | | | | | | | | | |
|---|---|---|---|---|---|---|---|---|---|
| 1 | Met | Ala | Thr | Leu | Ile | Ser | Thr | Thr | Ala | Ala |

|   |     |     |     |     |     |     |     |     |     |     |     |     |     |     |     |     |
|---|-----|-----|-----|-----|-----|-----|-----|-----|-----|-----|-----|-----|-----|-----|-----|-----|
| 1   | Met | Ala | Thr | Leu | Ile | Ser | Thr | Thr | Ala | Ala | Thr | Ala | Ala | Ser | 15  |
| 16  | Gly | Pro | Leu | Val | Asp | Tyr | Leu | Trp | Met | Ile | Leu | Gly | Phe | Ile | 30  |
| 31  | Ile | Ala | Phe | Val | Leu | Ala | Phe | Ser | Val | Gly | Ala | Asp | Val | Ala | 45  |
| 46  | Asn | Ser | Phe | Gly | Thr | Ala | Val | Gly | Gly | Val | Val | Thr | Leu | Lys | 60  |
| 61  | Gln | Ala | Cys | Ile | Leu | Ala | Ser | Ile | Phe | Glu | Thr | Val | Gly | Ser | 75  |
| 76  | Leu | Leu | Gly | Ala | Lys | Val | Ser | Glu | Thr | Ile | Arg | Lys | Gly | Leu | Ile | 90  |
| 91  | Asp | Val | Glu | Met | Tyr | Asn | Ser | Thr | Gln | Gly | Leu | Leu | Met | Ala | Gly | 105 |
| 106 | Ser | Val | Ser | Ala | Met | Phe | Gly | Ser | Ala | Val | Trp | Gln | Leu | Val | Ala | 120 |
| 121 | Ser | Phe | Leu | Lys | Leu | Pro | Ile | Ser | Gly | Thr | His | Cys | Ile | Val | Gly | 135 |
| 136 | Ala | Thr | Ile | Gly | Phe | Ser | Leu | Val | Ala | Lys | Gly | Gln | Gly | Gly | Val | 150 |
| 151 | Lys | Trp | Ser | Glu | Leu | Ile | Lys | Ile | Val | Met | Ser | Trp | Phe | Val | Ser | 165 |
| 166 | Pro | Leu | Leu | Ser | Gly | Ile | Met | Ser | Gly | Ile | Leu | Phe | Phe | Leu | Val | 180 |
| 181 | Arg | Ala | Phe | Ile | Leu | His | Lys | Ala | Asp | Pro | Val | Pro | Asn | Gly | Leu | 195 |
| 196 | Arg | Ala | Leu | Pro | Val | Phe | Tyr | Ala | Cys | Thr | Val | Gly | Ile | Asn | Leu | 210 |
| 211 | Phe | Ser | Ile | Met | Tyr | Thr | Gly | Ala | Pro | Leu | Gly | Phe | Asp | Asp | Lys | 225 |
| 226 | Leu | Pro | Leu | Trp | Gly | Thr | Ile | Leu | Ser | Val | Gly | Cys | Ala | Val | 240 |
| 241 | Phe | Cys | Ala | Leu | Val | Trp | Phe | Phe | Lys | Cys | Ser | Pro | Arg | Met | Lys | 255 |
| 256 | Arg | Lys | Ile | Glu | Arg | Glu | Val | Ile | Lys | Cys | Ser | Ser | Glu | Ser | Pro | 270 |
| 271 | Leu | Met | Glu | Lys | Lys | Asn | Ser | Leu | Lys | Glu | Asp | His | Gly | Glu | Thr | 285 |
| 286 | Lys | Leu | Ser | Val | Gly | Asp | Ile | Glu | Asn | Lys | His | Pro | Val | Ser | Glu | 300 |

```
301 Val Gly Pro Ala Thr Val Pro Leu Gln Ala Val Val Glu Glu Arg 315
316 Thr Val Ser Phe Lys Leu Gly Asp Leu Lys Glu Pro Gly Ala Arg 330
331 Glu Arg Leu Pro Ser Val Asp Val Lys Lys Glu Glu Thr Ser Ile Asp 345
346 Ser Thr Val Asn Gly Ala Val Gln Leu Pro Asn Gly Ile Asn Leu Val 360
361 Gln Phe Ser Gln Ala Val Ser Asn Gln Ile Asn Ser Gly His 375

376 Ser Gln Tyr His Lys Asp Ser Gly Leu Tyr Lys Glu 390
391 Leu Leu His Lys Leu His Leu Ala Lys Val Gly Asp Cys Met Gly 405
406 Asp Ser Gly Asp Lys Pro Leu Arg Arg Asn Ser Tyr Thr Ser 420
421 Tyr Thr Met Ala Ile Cys Gly Met Pro Leu Asp Ser Phe Arg Ala 435
436 Lys Glu Gly Gln Lys Gly Gly Met Glu Met Glu Lys Lys Leu Thr Trp 450

451 Pro Asn Ala Asp Ser Lys Arg Ile Arg Met Asp Ser Tyr Thr 465
466 Ser Tyr Cys Asn Ala Val Ser Ala Ala Leu His Ser Ala Ser Glu Ile 480
481 Asp Met Ser Val Lys Ala Met Gly Leu Gly Asp Arg Arg Lys Gly 495
496 Ser Asn Gly Ser Leu Gln Ser Tyr Asp Gln Asn Asp Lys Pro Glu 510
511 Val Ser Leu Leu Phe Gln Ile Leu Thr Ala Cys Phe 525

526 Gly Ser Phe Ala His Gly Asn Asp Val Ser Asn Ala Ile Gly 540
541 Pro Leu Val Ala Leu Tyr Leu Val Tyr Asp Thr Gly Asp Val Ser 555
556 Ser Lys Val Ala Thr Pro Ile Trp Leu Leu Tyr Gly Tyr Gly Val 570
571 Gly Ile Cys Val Gly Leu Trp Val Trp Gly Arg Arg Val Ile Gln 585
586 Thr Met Gly Lys Asp Leu Thr Pro Ile Thr Pro Ser Ser Gly Phe 600

601 Ser Ile Glu Leu Ala Ser Ala Leu Thr Val Val Ile Ala Ser Asn 615
616 Ile Gly Leu Pro Ile Ser Thr Thr His Cys Lys Val Gly Ser Val 630
631 Val Ser Val Gly Trp Leu Arg Ser Lys Lys Ala Val Asp Trp Arg 645
646 Leu Phe Arg Asn Ile Phe Met Trp Phe Val Thr Val Pro Ile 660
661 Ser Gly Val Ile Ser Ala Ala Ile Phe Arg Tyr Val 675

676 Ile Leu Arg Met Ter 680
```

| | | |
|---|---|---|
| 1 | GACGGTATCGATAAGCTTGATATCGAATTCCCTGTGCTCCACCTTGCACAGCGTTTGGGG | 60 |
| 61 | GACTGAAGACATAAGTGACGGGCGGGGGGGGGGGACTATGCGGAGTCCCAGGCTGCCC | 120 |
| 121 | TCTTCCCAGAGATGCGCCGCTATTGTTATTTTCTTCCACTTCGTCCCCCCAGGATGAACT | 180 |
| 181 | TGCGTCCTTTCTCTAATCCGCCATGGAATTCTGCTCCGTGCTTTTAGCCCTCCAGAGCCA | 240 |
| 241 | AAGAAACCCCAGACAACAGACGCCCAGACGCAGCAGCGTATAGCAGTAACTCCCCAGCTC | 300 |
| 301 | GGTTTCCGTGCCGTAGTTTACAGTATTTAATTTTATATAATATATACTATTTATTATAGC | 360 |
| 361 | ATTTTGATACCTCATTCCGTTTACACATCTCAAAAGCCGCTTAGTAATTCTCTTATTATT | 420 |
| 421 | TAAAGAACCACTACACTAGAGAATGGAATCTACTGTGGCAACGATTACTAGTACCCTAGC | 480 |
| 481 | TGCTGTTACTGCTTCCGCTCCACCGAAGTATGACAATCTATGGATGCTCATCCTGGGCTT | 540 |
| 541 | CATCATTGCATTTGTCTTGGCATTCTCCGTGGGAGCCAATGATGTAGCAAATTCGTTCGG | 600 |
| 601 | TACAGCTGTAGGCTCAGGTGTAGTGACCCTGAAGCAAGCCTGCATCTTAGCTAGCATCTT | 660 |
| 661 | CGAAACTGTGGGCTCCGCCTTGCTGGGGGCCAAAGTGAGCGAAACCATCCGGAACGGCTT | 720 |
| 721 | GATAGATGTGGAGCTGTACAACGAAACTCAAGATCTGCTCATGGCTGGCTCCGTCAGTGC | 780 |
| 781 | TATGTTTGGTTCTGCTGTGTGGCAGCTCGTGGCTTCGTTTTTGAAGCTTCCGATTTCTGG | 840 |
| 841 | GACCCATTGTATTGTCGGTGCAACCATTGGTTTCTCCCTTGTGGCAAATGGGCAGAAGGG | 900 |
| 901 | TGTCAAGTGGTCTGAACTGATAAAAATTGTGATGTCGTGGTTCGTCTCTCCGCTGCTTTC | 960 |
| 961 | TGGTATTATGTCTGGAATTTTATTCTTCCTTGTTCGTGCGTTCATCCTCCGTAAGGCAGA | 1020 |
| 1021 | TCCGGTTCCTAATGGCTTACGAGCTTTACCAATTTTTTATGCCTGCACAATCGGAATCAA | 1080 |
| 1081 | CCTCTTTTCCATTATGTATACTGGAGCACCGTTGCTGGGCTTTGACAAACTTCCTCTGTG | 1140 |
| 1141 | GGGTACCATCCTCATCTCGGTGGGATGTGCAGTTTTCTGTGCCCTTATCGTCTGGTTCTT | 1200 |
| 1201 | TGTATGTCCCAGGATGAAGAGAAAAATTGAACGAGAAGTAAAGTCTAGTCCGTCTGAAAG | 1260 |
| 1261 | TCCCTTAATGGAAAAGAAGAGCAACTTAAAAGAAGACCATGAAGAAACAAAGATGGCTCC | 1320 |
| 1321 | TGGAGACGTTGAGCATAGGAATCCTGTGTCTGAGGTAGTGTGTGCCACTGGGCCACTCCG | 1380 |
| 1381 | GGCTGTGGTGGAGGAGAGGACGGTGTCATTCAAACTTGGTGACCTGGAGGAGGCTCCGGA | 1440 |
| 1441 | GCGAGAGCGGCTTCCCATGGACCTGAAGGAGGAGACCAGCATAGACAGCACCATCAATGG | 1500 |
| 1501 | TGCAGTGCAGTTGCCTAATGGGAACCTTGTTCAGTTCAGTCAAACTGTCAGCAACCAGAT | 1560 |
| 1561 | CAACTCCAGTGGCCACTATCAGTATCACACCGTGCACAAGGATTCTGGCTTGTACAAGGA | 1620 |
| 1621 | GCTGCTCCATAAGTTACATCTGGCCCAAGGTGGAGACTGCATGGGAGATTCTGGGGACAA | 1680 |
| 1681 | GCCCTTGAGACGCAACAACAGCTACACTTCCTACACTATGGCAATATGTGGCATGCCCCT | 1740 |
| 1741 | GGATTCATTCCGTGCCAAAGAAGGTGAACAAAAGGGAGATGAAATGGAGACGCTGACATG | 1800 |
| 1801 | GCCTAATGCAGATACCAAGAAGCGGATTCGAATGGACAGTTACACCAGTTACTGCAATGC | 1860 |
| 1861 | CGTGTCTGACCTTCACTCCGAGTCTGAGATGGACATGAGTGTGAAGGCTGAGATGGGCCT | 1920 |
| 1921 | GGGTGACAGAAAGGAAGCAGTGGCTCTCTTGAAGAATGGTATGACCAGGATAAGCCTGA | 1980 |
| 1981 | AGTGTCCCTTCTCTTCCAGTTCCTGCAGATCCTTACAGCCTGCTTTGGGTCATTTGCCCA | 2040 |
| 2041 | TGGTGGCAATGACGTCAGCAATGCCATCGGCCCTCTGGTTGCTTTGTATCTTGTTTATAA | 2100 |

FIG.9A

```
       —+————+————+————+————+————+————+————+————+————+————+————+
2101   ACAAGAAGCCTCTACAAAAGCGGCAACACCCATATGGCTTCTGCTTTATGGTGGTGTTGG   2160
2161   CATTTGCATGGGCCTGTGGGTTTGGGGAAGAAGAGTTATCCAGACCATGGGGAAGGACCT   2220
2221   GACCCCAATCACACCCTCCAGTGGTTTCAGTATTGAACTGGCGTCTGCCTTAACTGTGGT   2280
2281   CATCGCATCAAACATTGGCCTTCCCATCAGCACAACACATTGCAAAGTGGGCTCTGTTGT   2340
2341   GTCTGTTGGCTGGCTCCGATCAAAGAAGGCTGTTGACTGGCGACTGTTTCGAAACATTTT   2400
       —+————+————+————+————+————+————+————+————+————+————+————+
2401   TATGGCCTGGTTTGTCACGGTCCCCATCTCTGGGGTTATCAGTGCCGCTATCATGGCAGT   2460
2461   ATTCAAGTACATCATCCTGCCAGTGTGACGCTGGGGTTGAAAGCTGTGTCAGTGTCTGGG   2520
2521   ACCATTGTACACATTCCTGTTCCTAGGAGAACGCTCACAGTGTTGCTGAAGACAGGCAAG   2580
2581   GGTCTTAAAGGAGCCGTGGGAAGGAAGTGTAATTTACACTATAATTGCTTTTGTGCTAAA   2640
2641   TATGACTTATCTCAAAATTAGCTATGTAAAATAGCCAGGTTTCCATTGATTCATTCCAAG   2700
       —+————+————+————+————+————+————+————+————+————+————+————+
2701   GTCCCTTTTCTCCTGGGCTATGAATTCCTGTACATATTTCTCTACTTTTGTATCAGGCCT   2760
2761   CAATTCCAGTATGTTTTAATGTTGTCTGTGAGATAACTTAGGTGGGTTCTTTTTAAACAG   2820
2821   CCAGCAGAGCCATTTGATGGCATGTACTGCTTTGTCGGCCTCACCAGCTTCTTCCCCAAC   2880
2881   ATGCACAGGGATTTAACAACATGTAACTGAAGCTTCCCTCCCTCATAGTCTCTCATAGAA   2940
2941   ATAGTCACGGCACTCTGCTCCCTGTCACTAGTGGCAGGTTCTGTTGATGTGTGACAACTT   3000
       —+————+————+————+————+————+————+————+————+————+————+————+
3001   CTTAGAGGGCCGAGAATCTTTGGCACAGTGGAAATATAAGTTTGTAGTAACCTCTTTGCA   3060
3061   AACAGTTCACGGACATGTTGCTAAGAAGCAGGGAGACAAAGCCCCTGGCCGGTTGTGGTTA   3120
3121   TTCTTCTGAGATTTCTGGCAGTGTGGGATGGGTGAATGAAGTGGAATGTGAACTTTGGGC   3180
3181   AAATTCAATGGGACAGCCTTCCATGTTCATCTGTCTACCTCTTAACTGAATAAAAAGCCT   3240
3241   ACAGTTTTTAAAAAAAAAAAA                                          3268
```

```
mouse Glvr-1 prot  VATITSTLAAVTASAPPKYDNLWMLILGFIIAFVLAFSVGANDVANSFGT
                  :AT:.:: :A.TA:: P  D LWMLILGFIIAFVLAFSVGANDVANSFGT
hum GLVR1 prot    MATLITSTTAATAASGPLVDYLWMLILGFIIAFVLAFSVGANDVANSFGT
                         ↑10      ↑20      ↑30      ↑40      ↑50 mouse Glvr-1 prot AVGSGVVTLKQACILASIFETVGSALLGAKVSETIRNGLIDVELYNETQD
                  AVGSGVVTLKQACILASIFETVGS.LLGAKVSETIR:GLIDVE:YN.TQ:
hum GLVR1 prot    AVGSGVVTLKQACILASIFETVGSVLLGAKVSETIRKGLIDVEMYNSTQG
                         ↑60      ↑70      ↑80      ↑90      ↑100 mouse Glvr-1 prot LLMAGSVSAMFGSAVWQLVASFLKLPISGTHCIVGATIGFSLVANGQKGV
                  LLMAGSVSAMFGSAVWQLVASFLKLPISGTHCIVGATIGFSLVA:GQ.GV
hum GLVR1 prot    LLMAGSVSAMFGSAVWQLVASFLKLPISGTHCIVGATIGFSLVAKGQEGV
                         ↑110     ↑120     ↑130     ↑140     ↑150 mouse Glvr-1 prot KWSELIKIVMSWFVSPLLSGIMSGILFFLVRAFILRKADPVPNGLRALPI
                  KWSELIKIVMSWFVSPLLSGIMSGILFFLVRAFIL:KADPVPNGLRALP:
hum GLVR1 prot    KWSELIKIVMSWFVSPLLSGIMSGILFFLVRAFILHKADPVPNGLRALPV
                         ↑160     ↑170     ↑180     ↑190     ↑200 mouse Glvr-1 prot FYACTIGINLFSIMYTGAPLLGFDKLPLWGTILISVGCAVFCALIVWFFV
                  FYACT:GINLFSIMYTGAPLLGFDKLPLWGTILISVGCAVFCALIVWFFV
hum GLVR1 prot    FYACTVGINLFSIMYTGAPLLGFDKLPLWGTILISVGCAVFCALIVWFFV
                         ↑210     ↑220     ↑230     ↑240     ↑250 mouse Glvr-1 prot CPRMKRKIEREVKSSPSESPLMEKKSNLKEDHEETKMAPGDVEHRNPVSE
                  CPRMKRKIERE:K.SPSESPLMEKK::LKEDHEETK:: GD:E:::PVSE
hum GLVR1 prot    CPRMKRKIEREIKCSPSESPLMEKKNSLKEDHEETKLSVGDIENKHPVSE
                         ↑260     ↑270     ↑280     ↑290     ↑300 mouse Glvr-1 prot VVCATGPLRAVVEERTVSFKLGDLEEAPERERLP-MDLKEETSIDSTING
                  V  AT PL:AVVEERTVSFKLGDLEEAPERERLP :DLKEETSIDST:NG
hum GLVR1 prot    VGPATVPLQAVVEERTVSFKLGDLEEAPERERLPSVDLKEETSIDSTVNG
                         ↑310     ↑320     ↑330     ↑340     ↑350
```

FIG. 10B

```
mouse Glvr-1 prot    AVQLPNGNLVQFSQTVSNQINSSGHYQYHTVHKDSGLYKELLHKLHLAKV
                         ↓360      ↓370      ↓380      ↓390      ↓400
hum GLVR1 prot       AVQLPNGNLVQFSQ:VSNQINSSGH QYHTVHKDSGLYKELLHKLHLAKV
                         ↑360      ↑370      ↑380      ↑390      ↑400 mouse Glvr-1 prot    GDCMGDSGDKPLRRNNSYTSYTMAICGMPLDSFRAKEGEQKGDEMETLTW
                         ↓410      ↓420      ↓430      ↓440      ↓450
hum GLVR1 prot       GDCMGDSGDKPLRRNNSYTSYTMAICGMPLDSFRAKEGEQKG: EME. LTW
                     GDCMGDSGDKPLRRNNSYTSYTMAICGMPLDSFRAKEGEQKGEEMEKLTW
                         ↑410      ↑420      ↑430      ↑440      ↑450 mouse Glvr-1 prot    PNADTKKRIRMDSYTSYCNAVSDLHSESEMDMSVKAEMGLGDRKGSSGSL
                         ↓460      ↓470      ↓480      ↓490      ↓500
hum GLVR1 prot       PNAD:KKRIRMDSYTSYCNAVSDLHS. SE: DMSVKA. MGLGDRKGS: GSL
                     PNADSKKRIRMDSYTSYCNAVSDLHSASEIDMSVKAAMGLGDRKGSNGSL
                         ↑460      ↑470      ↑480      ↑490      ↑500 mouse Glvr-1 prot    EEWYDQDKPEVSLLFQFLQILTACFGSFAHGGNDVSNAIGPLVALYLVY-
                         ↓510      ↓520      ↓530      ↓540      ↓550
hum GLVR1 prot       EEWYDQDKPEVSLLFQFLQILTACFGSFAHGGNDVSNAIGPLVALYLVY
                     EEWYDQDKPEVSLLFQFLQILTACFGSFAHGGNDVSNAIGPLVALYLVYD
                         ↑510      ↑520      ↑530      ↑540      ↑550 mouse Glvr-1 prot    KQEASTKAATPIWLLLYGGVGICMGLWVWGRRVIQTMGKDLTPITPSSGF
                         ↓560      ↓570      ↓580      ↓590      ↓600
hum GLVR1 prot       .:.S:K.ATPIWLLLYGGVGIC: GLWVWGRRVIQTMGKDLTPITPSSGF
                     TGDVSSKVATPIWLLLYGGVGICVGLWVWGRRVIQTMGKDLTPITPSSGF
                         ↑560      ↑570      ↑580      ↑590      ↑600 mouse Glvr-1 prot    SIELASALTVVIASNIGLPISTTHCKVGSVVSVGWLRSKKAVDWRLFRNI
                         ↓610      ↓620      ↓630      ↓640      ↓650
hum GLVR1 prot       SIELASALTVVIASNIGLPISTTHCKVGSVVSVGWLRSKKAVDWRLFRNI
                     SIELASALTVVIASNIGLPISTTHCKVGSVVSVGWLRSKKAVDWRLFRNI
                         ↑610      ↑620      ↑630      ↑640      ↑650 mouse Glvr-1 prot    FMAWFVTVPISGVISAAIMAVFKYIILPV
                         ↓660      ↓670      ↓680
hum GLVR1 prot       FMAWFVTVPISGVISAAIMA:F:Y:IL.:
                     FMAWFVTVPISGVISAAIMAIFRYVILRM
                         ↑660      ↑670
```

GIBBON APE LEUKEMIA VIRUS RECEPTOR

RELATED APPLICATIONS

This is a divisional of application Ser. No. 07/674,287 filed on Mar. 25, 1991, now U.S. Pat. No. 5,414,076, which is a continuation-in-part of application Ser. No. 07/398,351 filed on Aug. 24, 1989, now abandoned.

BACKGROUND OF THE INVENTION

The present invention relates to the receptor protein for gibbon ape leukemia virus, a retrovirus and to animal genes and their proteins which interact with gibbon ape leukemia virus (GALV). These GALV receptor proteins are required for entry of the virus into cells, and are therefore defined as cellular receptors for GALV.

Retroviruses can be placed into specified groups depending on the pathway used by the viruses to enter cells. It is thought that members of one given group utilize specific cellular receptors for entry into cells and that there is little, if any, cross-utilization of receptors by members of different groups. In general, these receptors have remained virtually unexplored. Of the approximately eight human receptors specific for the retroviruses known to infect human cells, only one has been cloned (CD4 for HIV; Maddon et al., 1986; McDougal et al., 1986). This invention therefore relates to one of the currently known receptors required for infection of animals, specifically human cells, by a retrovirus. Although the presence of a specific receptor protein for GALV (and for other retroviruses utilizing other receptor pathways) has been speculated, no GALV-specific receptor has heretofore been cloned or characterized.

While mention has been made of GALV, it is understood that simian sarcoma-associated virus and other viruses as stated above, utilize the same receptor (Weiss et al., 1984).

The novel genes and proteins of the present invention are useful in experimental manipulation of the GALV host, in analysis of virus/receptor interactions, and in elucidation and exploitation of the normal role of the receptor, which may include functions in substrate/ion transport and/or in immune activity.

BRIEF DESCRIPTION OF THE DRAWINGS

FIG. 3A Southern analysis of HindIII-digested human (H), transfectant (GRT), and mouse NIH3T3 (M) DNAs using the 5' EcoRI insert fragment of lambda HGR6 (subcloned in pUC118) as probe. FIG. 3B Southern analysis of EcoRI-digested DNAs using the middle EcoRI fragment of lambda HGR6 (subcloned in pUC118 as probe. FIG. 3C Northern analysis of oligo-dT-purified RNAs. Lane 1, NT2.1.1 RNA hybridized with a single-standard RNA probe derived from the 5' EcoRI fragment of lambda HGR6 and transcribed in the 3'–5' direction as indicated in FIG. 6A–C Lane 2 and 3 GRT-5 and NT2.1.1 RNAs hybridized with the three EcoRI inserts of lambda HGR6 (subcloned in pUC118) as probe.

FIGS. 6A–6C. DNA sequence of the human cDNA for the GALV receptor (SEQ ID NO:1). The long open reading frame extends from positions 371 to 2407, inclusively.

FIG. 7A and 7B. Amino acid sequence (SEQ ID NO:2) of the human GALV receptor protein, as derived from the long open reading frame in FIG. 5A and 6B (SEQ ID NO:1).

FIGS. 9A and 9B. Nucleotide sequence of Glvr-1 (SEQ ID NO:3). The sequence is a composite of pMGR1 (bases 1–2777) and pMGR2 (bases 1113–3260). The ATG and TAG codons defining the long open reading frame and the presumptive polyadenylation signal are underlined. EcoRI linkers added during cloning are not indicated.

FIGS. 10A and 10B. Comparison of the human and murine GALV receptor protein sequences (SEQ ID NOS:2 & 3) respectively) using the method of Needleman and Wunsch, 1970. In the sequence Listings, Xaa indicates the position of the stop codon.

SUMMARY OF THE INVENTION

Figure 4:
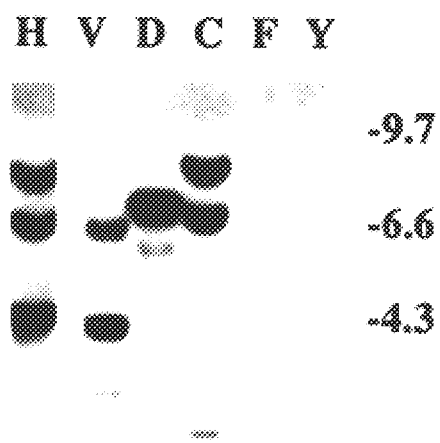
FIG. 4. Southern analysis of EcoRI-digested human (H), African green monkey vero cell (V), dog (D), cat (C), frog (F) and yeast (Y) DNAs using the 5' EcoRI insert fragment of lambda HGR6 (subcloned in pUC118) as probe.

The present invention relates to the GALV protein receptor and its homologs expressed in a wide variety of animal tissues. The primary amino acid sequence of the human receptor (SEQ ID NO:2) is illustrated in FIGS. 7A and 7B. However, as would be expected from the wide host range of GALV (Weiss et al., 1984) and from Southern analysis of species other than human (FIG. 4), closely-related homologs exist in species such as dog, cat, mouse and monkey, and others. The amino acid sequence of the corresponding mouse protein is provided in FIGS. 10A and 10B (SEQ ID NO:4). These observations support the universal existence of discrete genes truly homologous to the human GALV receptor. Thus, the present invention relates not only to the specific proteins identified in FIGS. 7A, 7B, 10A and 10B but also to proteins having substantially the same sequence and/or substantially the same capacity to allow viral infection as the protein illustrated in FIGS. 7A, 7B, 10A and 10B (SEQ ID NOS:2 & 4). Further, the invention relates to the purified DNA sequence (See, e.g., FIGS. 6A to 6C, 9A and 9B SEQ ID NOS:1 and 3) coding for the human (GALV) receptor (also referred to as GLVR1 [human] or Glvr-1 [mouse]) and to DNAs having substantially the same DNA sequence encoding substantially the same amino acid sequence as the DNA in FIGS. 6A to 6C, 9A and 9B (SEQ ID NOS:1 and 3). It is appreciated by those of ordinary skill in the art that other such proteins from other species, as well as other alternatives to the protein illustrated in FIGS. 7A, 7B, 10A and 10B (SEQ ID NOS:2 and 4) are isolated by the process of the present invention. Various expression systems may be used to produce varieties to those proteins but such varieties still result in a protein with similar biological activities to the present protein. It is also recognized by those skilled in the art that modifications to the DNA sequence presented in FIGS. 6A to C, 9A and 9B (SEQ ID NOS:1 and 3) results in GALV receptor proteins. The resultant DNA sequences and resulting proteins having substantially the same role in allowing viral entry are included within the scope of the invention. The biological function of the receptor is measured by infection studies of cells normally not infectable and transfected with constructs designed to express the protein (as demonstrated in Table 1). Further, antibody binding studies characterize and identify amino acid sequence and structure. Virus infection studies functionally identify a protein's role in allowing viral entry.

The GALV receptor proteins of the present invention are produced through expression vectors comprising a DNA sequence encoding a GALV receptor protein (including human, mouse or DNA sequences of the homologs of other species) or mutants (with or without the ability to confer susceptibility to infection on normally uninfectable cells) wherein one or more amino acids have been inserted, deleted, or substituted in or from the amino acid sequence of the human or mouse GALV receptor protein or of their homologs from other species. The invention also relates to biologically active fragments of the whole receptor protein, i.e., those portions of the molecule which confer binding ability, and/or antigenicity, and/or substrate/ion transport ability.

Additionally, the present invention includes a method for identifying GALV receptor homologs of all animal species wherein a DNA probe selected from the DNA in FIGS. 6A–C or 9A & B (SEQ ID NOS:1 and 3 or with substantially the same DNA sequence as that identified in FIG. 6 or 9 (SEQ ID NOS: 1 and 5), is used to isolate the appropriate DNA from the other species.

Further, as can be determined by those skilled in the art, the manipulation of the GALV receptor allows for regulation of viral entry into cells. This may allow the prevention of certain viral infections and the ability to control this mechanism for retroviruses utilizing the GALV receptor protein for cellular entry. The protein per se can be used to screen compounds which bind to the receptor. Such compounds can be used therapeutically to bind the receptor, thereby preventing viral entry at these sites. A therapeutically effective amount of a GALV-receptor binding agent is used to manipulate cellular infectivity for retroviruses. Additionally, the solubilized receptor, or biologically active fragment thereof, can be administered to a host so as to bind and inactivate virus.

For purposes of the present invention, the plasmids, DNA sequences, and microorganisms deposited in connection with the present invention, except where specified to the contrary, are deposited in American Cyanamid Company's culture collection maintained in Pearl River, N.Y. and are deposited with American Type Culture Collection in Rockville, Md. 20952, U.S.A.

Although the use of genetic engineering techniques lend themselves to effective methods to produce the GALV receptor proteins of the present invention, it is equally to be noted that the present proteins encompass other methods of production, such as chemical synthesis or purification from animal tissues. Isolation of the protein can be achieved by any of the protein purification methods known in the art.

It is an object of the present invention, therefore to provide the novel receptor protein of the GALV receptor. Also, the GALV receptor protein of other animal species, besides the human GALV receptor protein, is encompassed by the present invention. Another object of the invention is to provide an isolated DNA sequence coding for the GALV receptor. These and other objects of the invention will become apparent by the more detailed description of the invention provided hereinbelow.

DETAILED DESCRIPTION OF THE INVENTION

The present invention relates to the GALV receptor protein. The species analyzed in greatest detail is the human, but data relating to the mouse sequences are also provided, and it is recognized that similar proteins exist in other animal species. Therefore, the invention includes those homologous proteins from other species. The present invention discloses the structure of cDNA for the GALV receptor from human HL60 cells and mouse thymus cells. Further, the functionality of the isolated cDNA in allowing viral entry is provided in the following examples but is not limitative thereof.

The studies reported below allow a comparison of human GLVR1 to its mouse homologue, Glvr-1, and provide a general characterization of Glvr-1 RNA expression in murine tissues. Comparison of the presumed proteins encoded in the human and mouse cDNAs reveals a high degree of homology, the long open reading frames being almost identical in length and coterminal. The homology includes three potential N-linked glycosylation sites at positions 100, 374 and 418 (that at position 497 in the human is not present in the murine cDNA) and 12 of the 13 cysteine residues present in each protein. Two of these cysteines are found in what appears to be a repeated region within the protein which is fully conserved between the two cDNAs. This repeat spans the sequences Leu Pro Ile Ser Gly Thr His Cys Ile Val Gly (nucleotides 827–859 (SEQ ID NO: 3) and 743–775 (SEQ ID NO:1) in mouse and human cDNA, respectively) and Leu Pro Ile Ser Thr Thr His Cys Lys Val Gly (nucleotides 2300–2332 (SEQ ID NO:3) and 2222–2254 (SEQ ID NO:1) in mouse and human cDNA, respectively).

The positions at which the two proteins differ involve less than 10% of residues and many of these differences are conservative, having little or no effect on those regions of the protein which are highly hydrophobic and which are likely to represent transmembrane domains (O'Hara et al., 1990). The differences between the two proteins are not randomly distributed, being largely clustered in four groups. In order to define regions of the protein that are critical for infection, a series of clones is constructed by exchanging equivalent portions of human and murine cDNAS. These and several clones with deletions in GLVR1 are tested for their ability to confer susceptibility to infection. The results indicate that the terminal one-third of the protein is critical in controlling infectivity. The murine sequence differs from the human at three portions in this region, involving residues 553–560, 576 and 673–681 (SEQ ID NO:2). On the assumption that, of these three differences, residues 553–560 (SEQ ID NO: 2) are the primary determinants of permissivity because they are hydrophilic and therefore might be available for binding by virus, the murine cDNA is therefore altered by in vitro mutagenesis to encode the corresponding human residues in this region only. This construct is found to readily confer susceptibility to infection, and therefore identify residues 550–558 (SEQ ID NO:2) of GLVR1 as critical for infection by GALV.

In the region 5' to the long open reading frame, several ATG codons are present in both cDNAs. Those in the human cDNA have the potential to initiate translation of only short peptides (O'Hara et al., 1990) and, except for one, do not conform to the consensus sequence for initiation of translation. In addition, these ATG codons are dispensible for conferring the phenotype of sensitivity to infection, as we have shown here. The upstream ATG codons in the mouse cDNA also have the potential to initiate translation of only short peptides and only one (which is also conserved in the human) conforms well to the expected sequence for translation initiation. It is possible that these upstream open reading frames direct the translation of proteins with some as yet unknown function or may represent sequences involved in control of the expression of the GALV receptor protein. The present invention, therefore also encompasses these putative peptides and DNA sequences encoding them; the peptides are useful in production of antibodies, which in turn may be used in the study of the pattern of expression of the peptides in the cell.

Sequences conforming to the consensus sequence for polyadenylation are found at approximately the same positions in both cDNAs. Because the sequence in the murine cDNA is followed at 15 bases by a short polyA tract, these appear to be functional polyadenylation signals.

Glvr-1 RNA is detected at some level in almost all tissues. On the assumption that protein levels will generally reflect RNA levels, this suggests that the function of the gene is not peculiar to a specific cell type. This finding is in agreement with the sensitivity to infection in vitro of cells derived from a wide range of tissues (Weiss et al., 1984). Despite the widespread distribution of the RNA, the levels vary widely among different tissues. The level is by far highest in most compartments of the brain. Because internal capsule and brainstem are largely white matter and contain a level of RNA similar to those found in several other tissues (e.g., cortex) which are rich in gray matter, it appears that Glvr-1 expression is not favored in either white or grey matter. RNA levels are also found to be high in the thymus and in the spleen of an animal undergoing a graft-versus-host (GVH) reaction, where 60% of the spleen cells are constituted by activated graft cells. It may therefore be that T cells in vivo express high levels of Glvr-1. These findings of high levels of RNA in brain, thymus, and GVH spleen demonstrate a substantial degree of tissue-specificity in the expression of Glvr-1 and suggest that the protein may be particularly important in neurophysiology and in T cell function.

The locus is expressed at each stage of rat development in the tissues examined. A variation is found in whole embryos in early stages of embryo-genesis, there being a notable increase in RNA at the ten-day stage as compared to the eight-day stage. Thereafter the RNA levels in heads and brains declined slightly until after birth, where it is found that adult brain expresses more RNA than is present in fetal or neonatal brain. These results suggest that the level of Glvr-1 expression may have developmental consequences.

It has recently been shown that Glvr-1 is tightly linked to the genes for interleukin-1 (Il-1) and the prion protein (Prn-P) on mouse chromosome 2 and is likely to be proximal to Prn-P (Kaelbling et al., 1991). It is possible that Glvr-1 is related or even identical to other loci mapped to this area. This applies in particular to the minor histocompatibility antigens H-3 and H-42 (Ishikawa et al., 1986; Kurtz et al., 1985). These antigens are likely to be cell surface markers, as is Glvr-1, and are apparently widely-expressed, which is also the case, as has been shown here. The relationship between Glvr-1 and markers in its immediate vicinity, including the minor histocompatibility antigens and several genes involved in development, remains to be determined.

Although the normal physiological role of the GALV receptor gene has not previously been clear, the gene now appears to be homologous with Pho-4, a phosphate permease of *Neurospora Crassa* (Mann et al., Gene 83:281–289, 1989), incorporated herein by reference. The homology is sufficient to allow the presumption that the GALV protein also acts as a permease. As such, the protein, and heterologous cells expressing the protein, can be readily used to study the process of ion or substrate transport, and can serve as the basis of a screen for pharmaceutical products to control ion/substrate transport.

EXAMPLE 1

Isolation of GALV Receptor

Portions of the human receptor gene (GLVR-1) for gibbon ape leukemia virus (GALV) are isolated in the following manner. Firstly, DNA from human cells (which are easily infected with GALV and therefore express that viral receptor) are introduced into mouse NIH3T3 cells (which cannot be infected with the virus) in one of a variety of ways, the procedure of $CaPO_4$ precipitation being described below. High molecular weight human DNA is mixed with pSV2gpt in aqueous solution containing $CaCl_2$ and the mixture is added to a second solution containing phosphate and HEPES buffer at pH 7.1. The DNAs precipitate together in aggregates with $CaPO_4$ and this aggregate is applied to cells in culture (mouse NIH3T3 cells). A portion of the cells takes up aggregates of the DNA mixture and incorporates and expresses the transfected DNA.

In order to study only those cells which have been transfected, selection is imposed for the presence of pSV2gpt. To do this, cells are grown in medium containing mycophenolic acid and zanthine. The mycophenolic acid imposes a metabolic block on the cells which can be overcome by the expression of guanosine phosphoribosyltransferase (encoded by pSV2gpt) through its utilization of xanthine (Mulligan and Berg, 1981). After about two weeks in this medium, only transfected cells remain. A given cell in this culture now expresses approximately 0.1% of the human donor DNA. A portion of these (approximately 1/1000) are expected to express the human receptor for GALV. Such cells are isolated by infection with an antibiotic-resistant virus which requires interaction with the GALV receptor to enter cells. This virus is made by rescuing pGV16, a G418-resistant, replication-defective virus (Noda et al., 1986) from cells, using GALV, such that the pGV16 pseudotyped by GALV (i.e., the pGV16 RNA genome is contained in a GALV particle). The mixture [termed pGV16 (GALV)] can now only infect cells using the pathway regularly used by GALV. This mixture is applied to the transfected mouse cells and these are treated two days later with G418 antibiotic. Only cells infected with pGV16 survive. These are termed primary transfectants and should contain approximately 0.1% of the human genome in each independent isolate.

EXAMPLE 2

Transfection

The transfected material found in the primary transfectants will contain a large amount of human repetitive sequences and should also include the human GALV receptor gene. However, because the pressure for the maintenance of the gene is lost after infection with virus and selection for pGV16, many transfectants can be expected to have segregated the gene, as is normal for any such experiment. For this reason, a primary transfectant is sought which has been infected with pGV16 but not with the replication competent GALV. The continued presence of the receptor, and therefore of the receptor gene, can be demonstrated in such a cell because it is not immune to superinfection as are cells which have been infected with GALV. These constitute the majority of isolates because GALV is in excess over pGV16 in the pGV16(GALV) stocks. A transfectant infected only with pGV16 is chosen, in this case the cell termed GRT5, DNA is prepared from it, and the DNA used in a second round of transfection to obtain secondary transfectants. The process to obtain these is similar to that used to derive primary transfectants. That is, DNA from GRT5 is mixed with pSV2gpt, precipitated with CaPO$_4$, and transfected into NIH3T3 cells. These are then grown in medium containing mycophenolic acid and zanthine and the surviving cells are infected with pGV16(GALV). G418 is then applied and surviving cells are grown up and examined to identify presumptive secondary transfectants for the receptor gene. Since proviral pGV16 is present in the primary donor DNA, some of the secondary transfectants will have become G418-resistant from transfection of the proviral DNA. The bona fide receptor transfectants can, however, be distinguished from these because the majority of the secondary transfectants are therefore screened for GALV production and DNA is prepared from any found. This DNA is analyzed in Southern analysis to determine if any of the producers contain human repetitive sequences. Because the processes of primary and secondary transfection successively reduce the amount of human repetitive DNA to be found in a transfectant, it is expected that any repetitive human DNA found in a secondary transfectant is specifically associated with the receptor gene.

EXAMPLE 3

Isolation of cDNA and cDNA Probes

Figure 1:
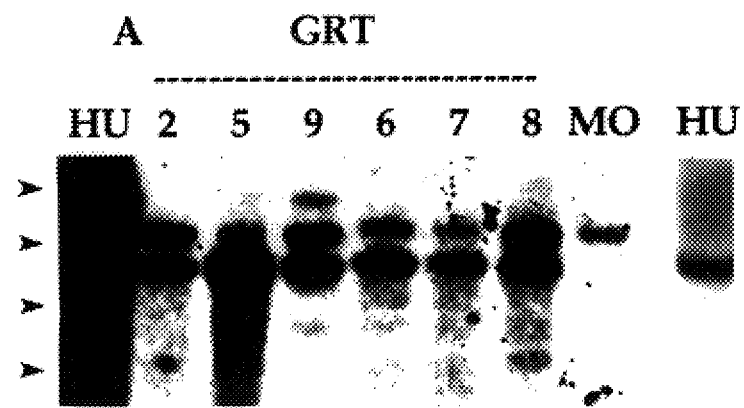
FIG. 1. Southern analysis of human (HU) transfectant (GRT), and mouse (MO) BamHI-digested DNAs. The left panel shows a blot hybridized with the entire (repeat-containing) 3.5 kb EcoRI insert of pR7h. The right lane is hybridized with the 2.2 kb EcoRI-HindIII subfragment.

A genomic library is constructed from any such secondary transfectants found in Example 2 (in this case GRT9, the secondary transfectant, and lambda gt10 and EcoRI as the vector and cloning enzyme, respectively) and screened for the presence of clones containing human repetitive DNA using human DNA made radioactive in nick translation as probe. One in 500,000 clones is found to hybridize with the probe. This clone (lambda R7h) is plaque-purified to homogeneity and its 3.5 kb EcORI insert is cloned in pGEM2 and pUC118. This 3.5 kb EcoRI fragment is found to consist of 2.2 and 1.3 kb EcoRI-HindIII fragments. Use of the entire 3.5 kb fragment as probe in Southern analysis demonstrates that the cloned DNA contains human repetitive sequences, as expected, and that it hybridizes to a 6.6 kb EcoRI fragment in most of the transfectants but not appreciably to mouse DNA (FIG. 1, longer exposure times reveal the presence of a hybridizing band in mouse DNA representing the murine homolog, as expected). The presence of this latter transfected sequence in independent transfectants demonstrates that the sequences in lambda R7h are part of or are in close proximity to the receptor gene. Use of the 2.2 kb fragment as probe gives the same result except that in human DNA only a single fragment of 6.6 kb is detected (FIG. 1). This indicates that only single copy sequences are contained in this fragment.

Figure 2:
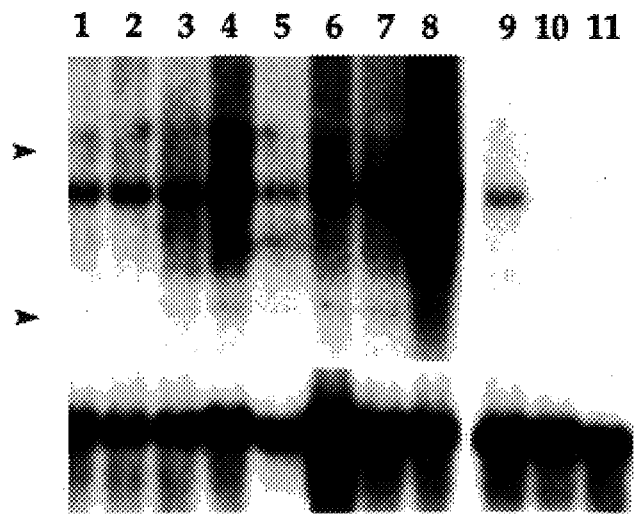
FIG. 2. Northern analysis of human, transfectant, and mouse RNAs. Probes used are the 2.2 kb EcoRI-HindIII subfragment of pR7h (upper panel) and an actin probe (lower panel; O'Hara et al., 1987). Lanes 1–4, total cellular oligo-dT purified RNA of the human cell line TU1.1.1 (O'Hara et al., 1987) Lane 1, confluent cells. 2, log-phase. 3, confluent GALV-infected. 4, confluent Mo-MuSV (GALV)-infected. Lanes 5–8, total cellular oligo-dT purified RNA of the human cell line NT2.1.1 (O'Hara et al., 1987). Lane 5, confluent. 6, log-phase. 7, confluent GALV-infected. 8, confluent Mo-MuSV(GALV)-infected. 9–11, cytoplasmic oligo-dT purified RNAs of primary transfectant GRT5, secondary transfectant GRT9, and NIH3T3 cells. resp.
Figure 5:
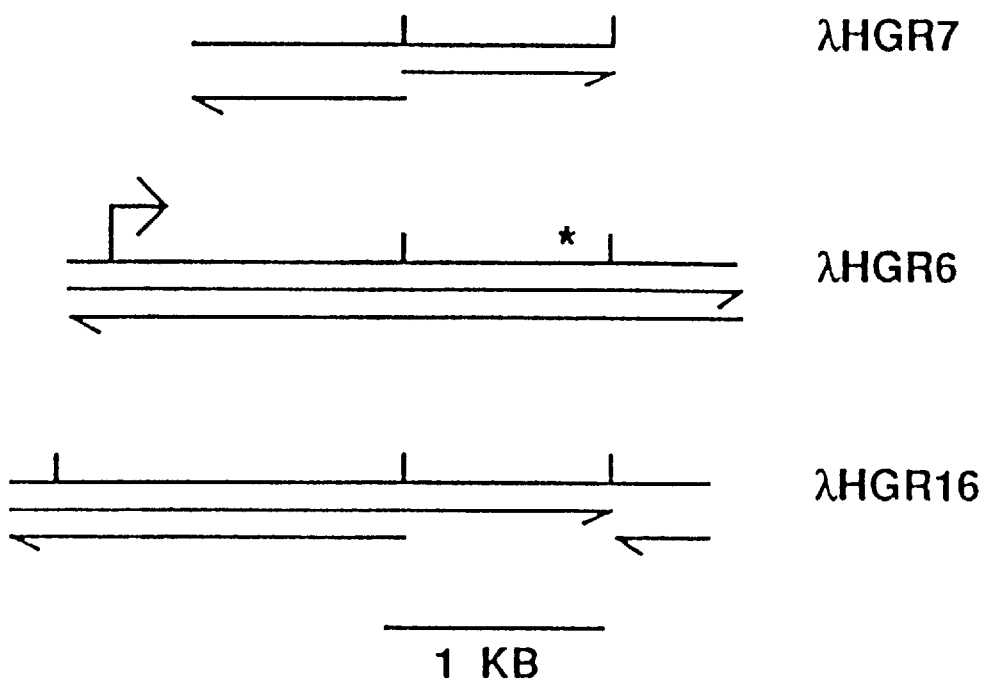
FIG. 5. Human cDNAs isolated and the strands sequenced. Notches represent EcoRI sites. EcoRI linkers are present at each end of each clone where no notch is indicated. The long open reading frame is indicated for lambda HGR6 by the arrow (translation start) and asterisk (termination codon).

When this fragment is used as probe in northern analysis, a single mRNA of approximately 4 kb is detected in human cells and in GRT5, the transfectant with the highest copy number for the transfected DNA; no strongly hybridizing RNA is found in mouse cells (FIG. 2). This indicates that the cloned sequences are expressed in RNA and are therefore suitable for screening cDNA libraries. Accordingly, a cDNA library from human HL60 cells (obtained from Clontech, #HL1020b) is screened with the fragment and 1/10,000 plaques are found to hybridize. Three of these (lambda isolates HGR6, HGR7, and HGR16, FIG. 5) are purified and the EcoRI fragments contained are subcloned in pUC118 and sequenced using the dideoxy termination method.

Analysis of the sequences reveals several features.
1. The sequences of the clones are virtually identical.
2. Lambda HGR6 and lambda HGR16 contain a single large open reading frame of 679 amino acids each, the presumptive amino acid sequences of which are identical.
3. Lambda HGR7 appears to be a truncated cDNA in that it contains a large open reading frame with an identical presumptive amino acid sequence for the 3' two-thirds of the presumptive protein encoded by the above isolates starting at amino acid 180 in FIGS. 7A & B (SEQ ID NO:2).
4. The presumptive protein encoded by these isolates (FIGS. 7A & B) (SEQ ID NO:2), has the characteristics of an integral membrane protein. That is, analysis by the program of Kyte and Doolittle (1982) indicates several regions as possible membrane-spanning domains (these are approximately residues 15–39, 159–182, 228–251 and 651–674) (SEQ ID NO:2). Other regions are also hydrophobic, though to a lesser degree, and may also represent membrane-spanning domains (for example, regions 56–79, 118–141 and 555–578) (SEQ ID NO:2). The similarity of the presumed protein to integral membrane proteins is in keeping with its expected function as a retroviral receptor.

Figure 3A:
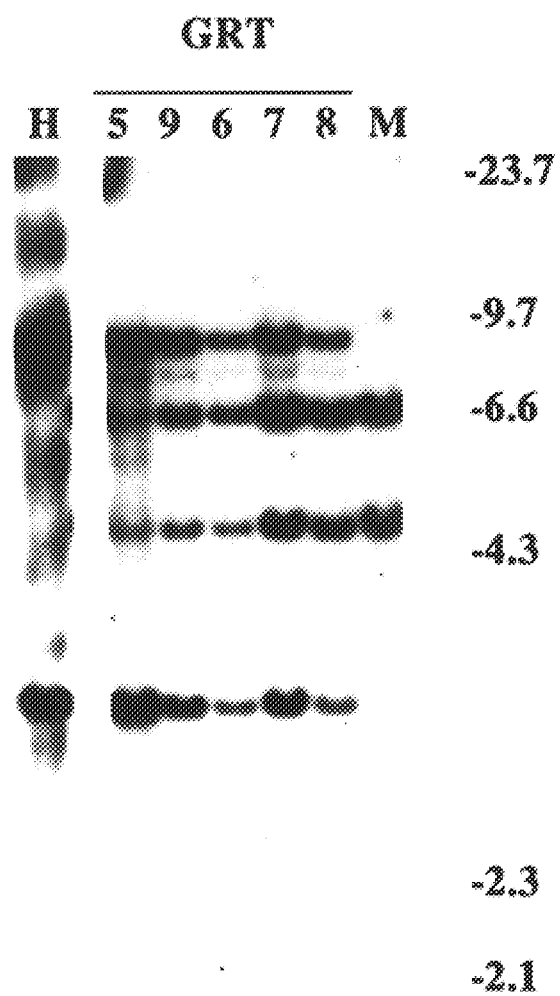
FIGS. 3A to 3C Southern and Northern analysis using cDNA probes.
Figure 3B:
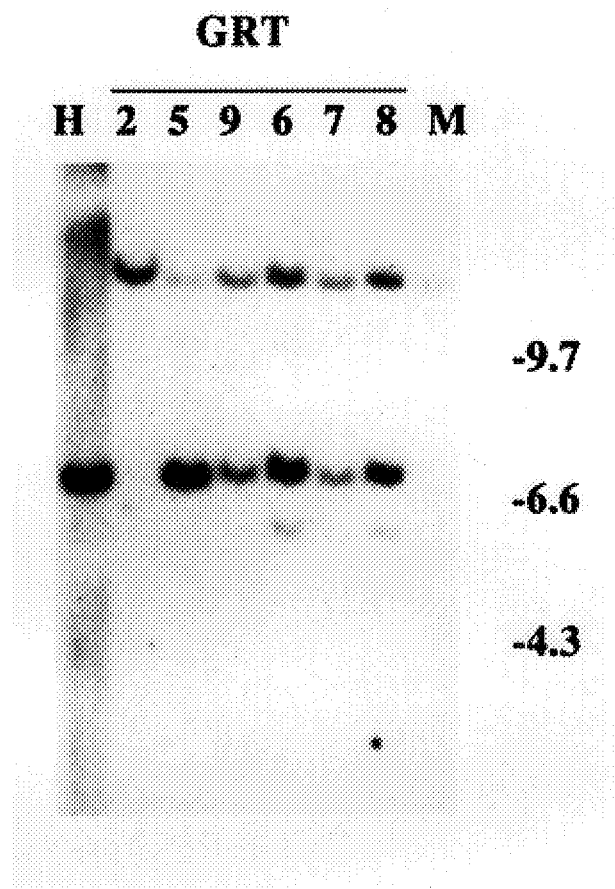
Figure 3C:
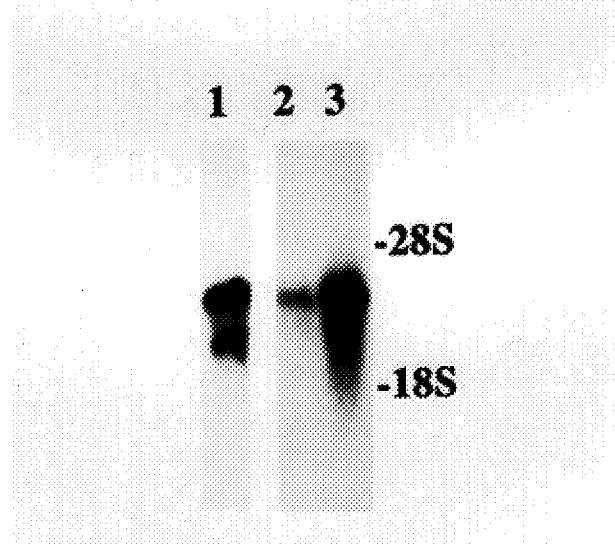

To further characterize the isolates, EcoRI fragments subcloned from lambda HGR6 are used in Southern analysis of human, transfectant and mouse DNAs. It is found that all fragments detected in human DNA are also found in transfectant DNAs but not in mouse DNA (FIG. 3A, B). This further confirms that the isolates are derived from the receptor gene because such a great length of sequence would not be found in independent transfectants unless its presence had been selected for. FIG. 3C shows that the expected RNA is detected using cDNA probes.

EXAMPLE 4

Expression

Figure 8:
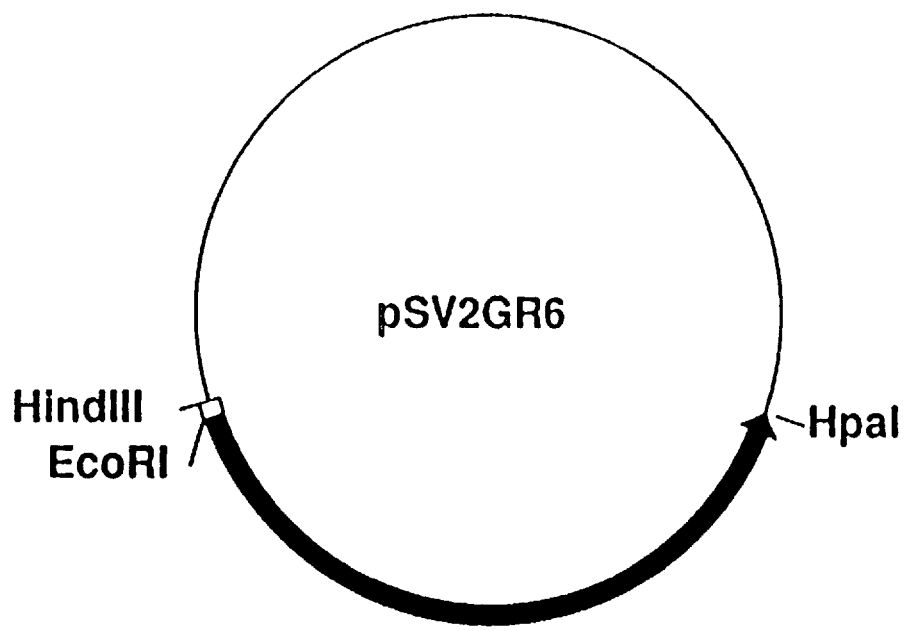
FIG. 8. Structure of pSV2GR6. The thin black line represents sequences derived from pSV2gpt. The small box represents sequences derived from the multiple cloning site of pUC118, and the arrowed box represents sequences derived from the insert of lambda HGR6. For this construction, lambda HGR6 is digested partially with EcoRI and the three contiguous EcoRI inserts are isolated as a single fragment. This is then cloned at the EcoRI site in pUC118 (to give HGR6-1), so that the presumed 5' end of the insert is proximal to the HindIII site in pUC118. The portion of this plasmid between the HindIII and HpaI sites is cloned between the HindIII and HpaI sites of pSV2gpt to give pSV2GR6.

The ultimate proof that lambda HGR6 encodes the GALV receptor is derived by demonstrating its potential to confer susceptibility to GALV infection on mouse cells. pHGR6-1, containing the three EcoRI insert fragments of lambda HGR6 in the proper orientation, is digested with HindIII, which cuts in the multiple cloning site of the pUC118 vector at the 5' end of the insert, and with HpaI, which cuts in the 3' untranslated region of the insert. This fragment is used to replace the region of pSV2gpt between the HindIII and HpaI sites. The resulting plasmid, pSV2GR6 (FIG. 8), contains the entire open reading frame encoding the receptor with the SV40 early promoter upstream and an SV40 polyadenylation signal downstream. Mouse cells transfected with this plasmid are rendered susceptible to GALV infection, providing final confirmation that the clone does in fact encode the GALV receptor. Using the infectious center assay, up to 1% of the cells transfected with pSV2gpt and pSV2GR6 and selected for the presence of pSV2gpt are found to be infectable.

The plasmid pSV2GR6, containing the human GLVR-1, is deposited in the American Type Culture Collection located at 12301 Parklawn Drive, Rockville, Md. 20852 U.S.A., identified as "*Escherichia coli* DH5alpha, pSV2GR6," under deposit number ATCC 68070 (Aug. 2, 1989).

TABLE 1

Expression of pSV2GR6 Renders Mouse MIH3T3 Cells Susceptible to Infection by GALV

| DNA Transfected | IC[a] | G418[R] No Virus | colonies[b] pGV16 (GALV) |
|---|---|---|---|
| pSV2gpt | 0/10[5] | ND | 0/10[6] |
| pSV2gpt + pSV2GR6 | 739/10[5] | 0/10[7] | 252/6 × 10[6] |

Notes
[a]Number of cells producing virus/number tested. NIH3T3 cells (transfected and then grown in medium containing mycophenolic acid) were exposed to pGV16 (GALV) and plated with PG4 cells in an infectious center assay.
[b]Colonies formed in medium containing G418/number tested. NIH3T3 cells (transfected and then grown in medium containing mycophenolic acid) were plated in the presence of G418 after exposure, where indicated, to pGV16 (GALV)
ND Not Done

EXAMPLE 5

Cloning of Murine Glvr-1

A mouse thymus library (Stratagene 935303) in λ ZAP was screened with two EcoRI fragments containing bases 1–2659 (SEQ ID NO:1) of the human GLVR1 cDNA-containing clone pHGR6-1 (O'Hara et al., 1990). Hybridizing phage were plaque-purified and their inserts were excised in pBluescript SK⁻ (Stratagene) by co-infection with helper phage, as described by the manufacturers. Sequencing was performed using single-stranded DNA templates and synthetic oligonucleotide primers (Vieira and Messing, 1987; Banter et al., 1977).

Seven cDNA clones are obtained after screening of 50,000 plaques from a mouse thymus library with a GLVR1-specific probe. One of these (pMGR1) contains an entire open reading frame similar to the open reading frame in the human cDNA and a substantial portion of upstream sequence. pMRG2 contains most of the open reading frame and, apparently, all of the 3' untranslated sequence, as it has a short poly A stretch 15 bases after a polyadenylation signal. FIGS. 9A & B (SEQ ID NO:3) shows a composite of the sequences from pMGR1 and 2. It can be seen that Glvr-1 has the potential to encode a protein of 681 amino acid residues in its longest open reading frame (which is very similar in length to the presumed 679 residue human protein). An ATG codon closely resembling the consensus sequence for translation start (Kozak, 1986) initiates the open reading frame. Upstream of this codon, four other ATG codons are found (at positions 100, 132, 174 and 203) (SEQ ID NO:3). Those at positions 100 and 132 (SEQ ID NO:3) are not conserved in the human cDNA, do not closely fit the translation start sequence, and have the potential to initiate coding for peptides of only 25 and 31 residues, respectively. The ATG codon at position 174 (SEQ ID NO:3) is conserved in the human (position 106), (SEQ ID NO:1) fits the consensus sequence poorly in the human and only moderately well in the murine cDNA, and can direct synthesis of peptides of only 17 residues (almost identical in sequence) in each species. The ATG at position 203 (SEQ ID NO:3) in the murine is conserved relative to the human (position 135, (SEQ ID NO:1) in the human) and fits the translation start consensus sequence well in both species. Translation from these ATG codons would give similar peptides of 25 (human) and 26 (murine) residues. In the human sequence, at position 192 (SEQ ID NO:1) is an ATG codon encoding a six amino acid peptide with no corresponding murine peptide. The presence of polyadenylation signal sequences in the 3' regions of both human and mouse cDNAs, (followed in the mouse cDNA by a short polyA stretch) identifies the signal which is likely to be used in both species. Overall, the DNA sequence homology between the human and mouse cDNAs is approximately 90%.

FIG. 10 shows the presumed protein sequence of Glvr-1 and a comparison of the murine and human protein sequences (SEQ ID NOS:2 and 4). The two proteins differ at less than 10% of residues. The residues which differ are distributed throughout the protein but show a tendency to cluster in four areas. There is a region of considerable variation between the two proteins at the amino terminus. Residues 291–313 differ considerably from those in the human protein. In the carboxy-terminal third, two areas are substantially different: residues 553–561 and 673–681 in the murine cDNA (SEQ ID NO:3) compared to 550–558 and 671–679 in the human cDNA (SEQ ID NO:1).

The plasmid pOJ19, containing the full-length mouse glvr-1 sequence, is deposited with the American Type Culture Collectiion located at 12301 Parklawn Drive, Rockville, Md. 20852, U.S.A., identified as "*Escherichia coli* MC 1061 P3 harboring plasmid pOJ19," under deposit number ATCC 68517 (Jan. 24, 1991).

EXAMPLE 6

Definition of the Minimal Open Reading Frame Conferring Sensitivity to Viral Infection As mentioned, both human and mouse cDNAs contained ATG codons upstream of the codon initiating the long open reading frame. In order to assess their significance, it is necessary to test the effect on function of removing them. The only known function associated with the locus is the ability to confer sensitivity to infection by GALV and only the human cDNA will achieve this. Therefore, pOJ9, encoding the human cDNA but lacking ATG codons upstream of that initiating the long open reading frame, is constructed and tested for the ability to confer sensitivity to infection on mouse cells.

The construct is made in which the ATG codons normally present in the cDNA upstream of the ATG initiating the long open reading frame were removed. The sequence CATCTT (bases 318–323 in the human cDNA; O'Hara et al., 1990) is changed to the HindIII recognition sequence, AAGCTT, by in vitro mutagenesis. The HpaI site at position 2490 is changed to a BglII site by linker addition. The HindIII-BglII fragment is cloned into the eukaryotic expression vector, pcDNA1 (Invitrogen), between the HindIII and BamHI sites. This vector therefore carries the long open reading frame of GLVR1 cDNA under control of a cytomegalovirus promoter.

To test pOJ9, NIH3T3 cells, plated one day previously at $3 \times 10^5/60$ mm dish, are transfected with 1 µg pSV2neo or with pSV2neo and 3 µg pOJ9 or pSV2GR6 and carrier to 20 µg total DNA per dish, using $CaPO_4$ precipitation. pSV2neo confers resistance to the antibiotic G418 (Southern and Berg, 1982). pSV2GR6 contains the entire human GLVR1 cDNA, including the region with the three ATG codons upstream of the ATG initiating the long open frame, under control of the SV40 promoter (O'Hara et al., 1990). Three dishes are transfected with each precipitate. After two days, the cells are replated in medium containing G418 and colonies are allowed to form. Each of the nine dishes gives 80–200 colonies. Colonies derived from each dish are pooled and replated in each of two 60 mm dishes at $10^5$/dish with 4 µg/ml Polybrene (Sigma). After one day, one dish from each pool is exposed to 1 ml of GALV ($10^6$/ml). After a further two days, $10^4$ cells from each pool are replated with $3 \times 10^5$ PG4 $S^+L^-$ indicator cells (Haapala et al., 1985). The small proportion of viruses used for the infection surviving to this stage are destroyed by trypsinization prior to replating with the indicator cells. Foci initiated by productively-infected NIH3T3 cells are counted after five days cocultivation with PG4 cells.

Table 2 shows that NIH3T3 cells, which are not normally susceptible to infection by GALV, become susceptible after transfection with pOJ9. The efficiency with which this is achieved is no less than, and in fact slightly better than, the results obtained with pSV2GR6. This plasmid contains most of the GLVR1 cDNA, including the three upstream ATG codons, and has been previously shown to confer sensitivity to infection by GALV (O'Hara et al., 1990). This result establishes that expression of the protein from the first ATG in pOJ9, without the potential for co-expression of the small upstream open reading frames, confers the phenotype of sensitivity to infection.

TABLE 2 pOJ9 Renders NIH3T3 Cells
Sensitive to Infection by GALV

| Plasmid | Foci/3 × 10⁴ Cells | |
|---|---|---|
| | No GALV | GALV |
| pSV2neo | Not Done | 0 |
| pSV2neo + pSV2GR6 | 0 | 382 |
| pSV2neo + pOJ9 | 0 | 1000 |

NIH3T3 cells were transfected with the indicated plasmids and selected in G418. Pooled colonies were exposed to virus and tested for infection using indicator cells as described above.

EXAMPLE 7

Glvr-1 RNA Levels in Mouse Tissues

In order to study Glvr-1 RNA levels in mouse tissue, total RNA is prepared from quick-frozen and disrupted tissues as described (Glisin et al., 1974) and subjected to northern analysis. Hybridization is carried out in 50% formamide, 5×BSC, 5×Denhardt's, 0.1% SDS, and 200 µg/ml sonicated, denatured salmon sperm DNA, at 42° C. The probe used is the entire pMGR1 labeled by nick translation using $^{32}P$ dCTP. Washing is to a final stringency of 0.1×BBC, 0.1% SDS, at 65° C. For most mouse tissues, C57 BL6×DBA/2 $F_1$ hybrids are used. For spleen undergoing a graft-versus-host reaction, an $F_1$ hybrid is injected with $5 \times 10^6$ C57 BL6 spleen cells and the host spleen is removed for RNA preparation eight days after injection. Rat tissues are from Sprague-Dawley rats and are prepared at the developmental stages indicated in the figures.

Figure 11:
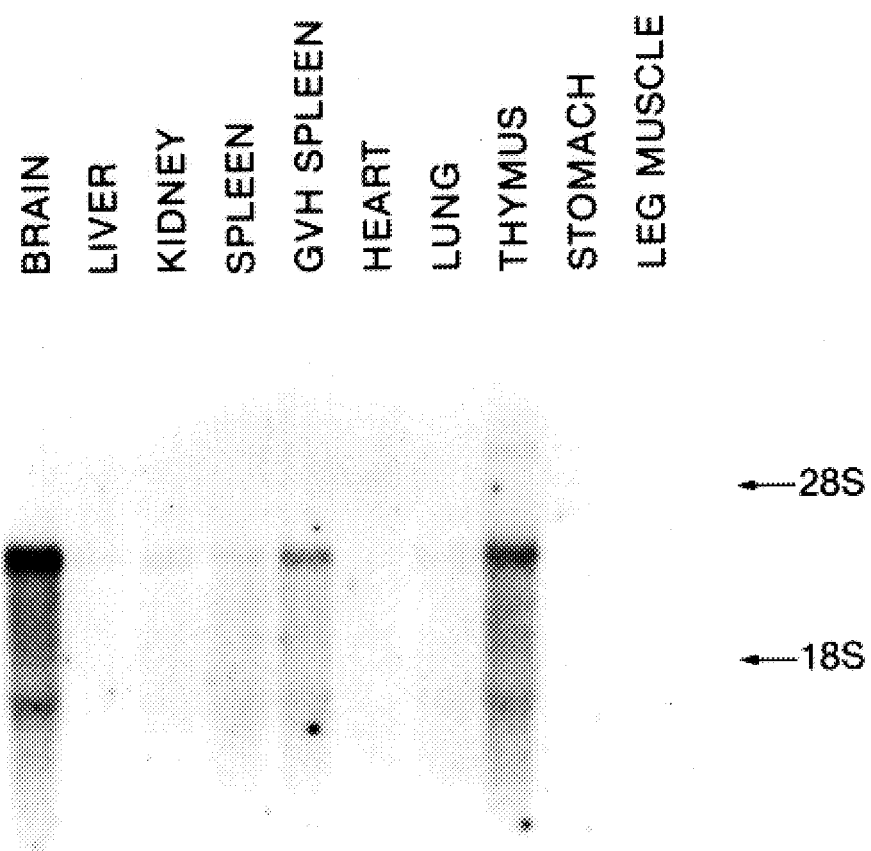
FIG. 11. Northern analysis of Glvr-1 in mouse tissues.

FIG. 11 shows that, using pMGR1 as probe, a single RNA species is readily detected in most tissues. Longer exposures allows detection of this RNA in all tissues examined except perhaps stomach. Despite the widespread presence of the RNA, there is considerable variation in level between tissues. The brain contains by far the highest levels, being several-fold higher than the next highest tissue, which is thymus. Spleen undergoing a graft-versus-host reaction (in which 60% of the cells are activated donor T cells) has a level of RNA approaching that found in the thymus.

Figure 12:
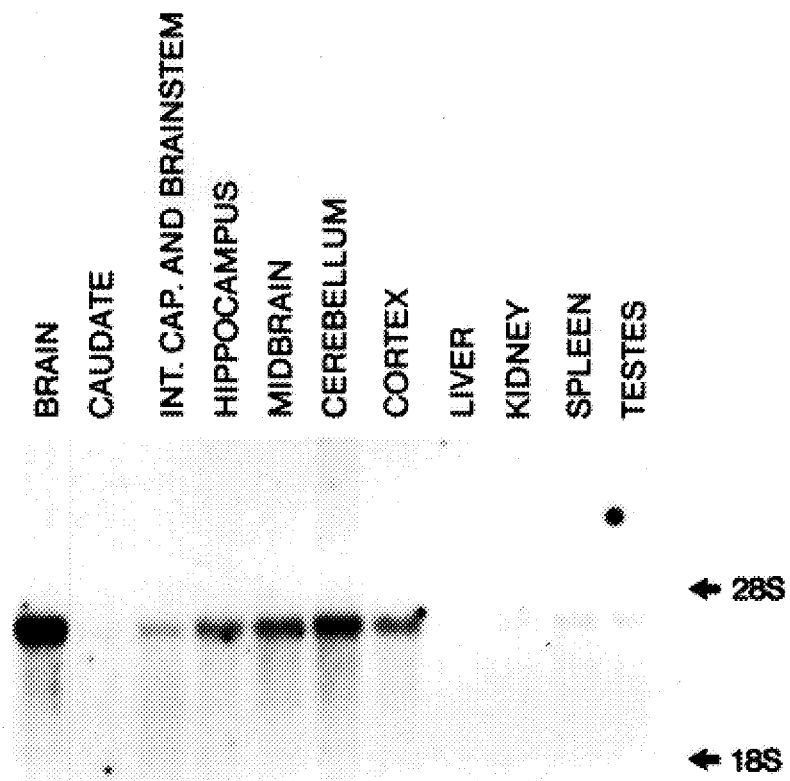
FIG. 12. Northern Analysis of Glvr-1 in rat tissues. Total brain was derived from a single rat. All compartments of brain were also derived from a single rat.

To determine which portion of brain expresses high levels of RNA, all compartments of brain are analyzed individually. FIG. 12 shows that the RNA is found at a high level in rat brain in comparison to other tissues, mirroring the results found with mouse tissues. Within the brain, RNA levels are found to be high in most compartments, notably so in hippocampus, midbrain, cerebellum, and cortex. The caudate nucleus, in contrast, expresses low levels of Glvr-1 RNA.

Figure 13:
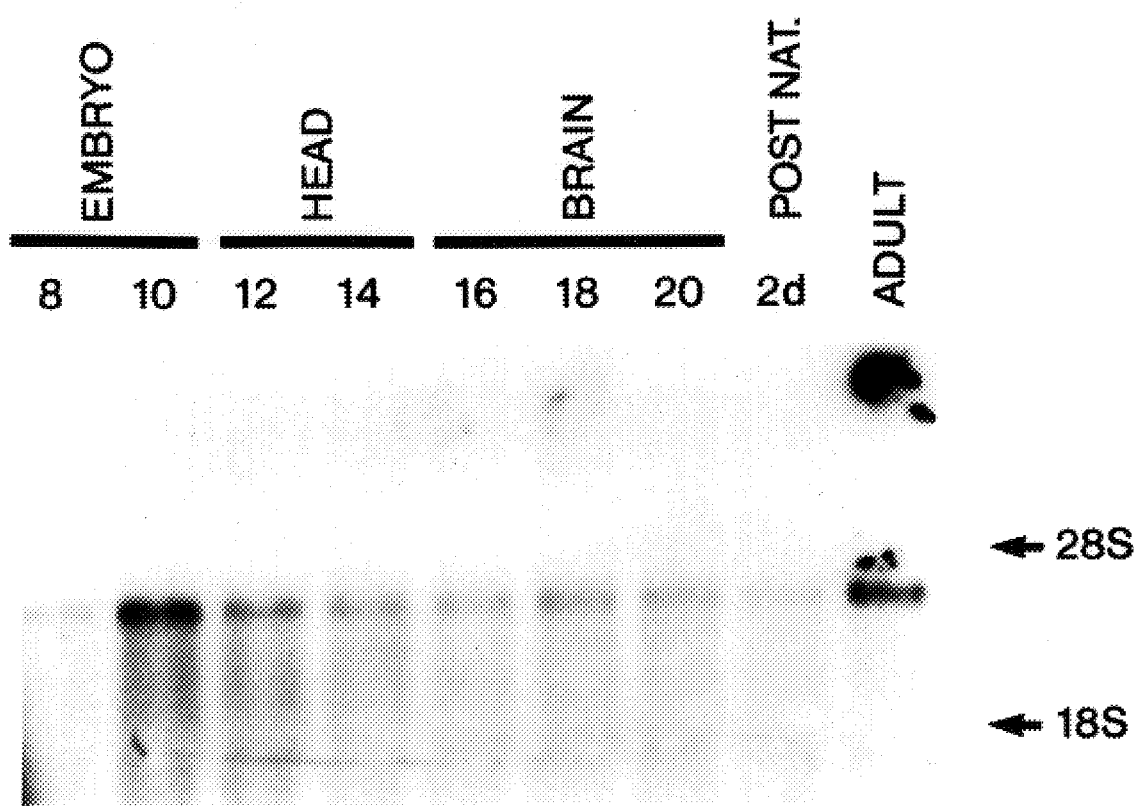
FIG. 13. Northern analysis of Glvr-1 in tissues of the rat taken at various stages of development. Whole embryos, heads, or brains were taken at the indicated days. Adult brain was from a 2-month-old rat.

In order to examine Glvr-1 expression during development, RNA levels are analyzed at several stages of rat embryogenesis. As can be seen in FIG. 13, the RNA is expressed at day 10 much more abundantly than at day 8 of development of whole rat embryos. No fluctuation is found when whole heads are analyzed at days 12 and 14, nor (except for a gradual decline) when whole brains are taken at days 16, 18, and 20 and two days after birth. A higher level of RNA is found in 2-month-old adult brain as compared to the later stages during embryogenesis.

BIBLIOGRAPHY

Glisin, V.; Crkvenjov, R.; and Byus, C. Ribonucleic acid isolated by cesium chloride centrifugation. Biochemistry, 13:2633–2639 (1974).

Haapala, D. K.; Robey, W. G.;Oroszlan, S. D.; and Tsai, W. P. Isolation from cats of an endogenous type C virus with a novel envelope glycoprotein. J. Virol, 53:827–833 (1985).

Ishikawa, H.; Hind, T.; Kato, H.; Suzuki, H.; and Saito, K. Cytotoxic T lymphocyte response to minor alloantigen in H-42b mice; clonal inactivation of the precursor cytotoxic T lymphocytes by veto-like spleen cells that express the H-42a antigen. J. Immunol 137:2080–2088 (1986).

Kaelbling, M.; Eddy, R.; Shows, T. B.; Copeland, N. G.; Gilbert, D. J.; Jenkins, M. A.; Klinger, H. P.; and O'Hara, B. Localization of the human gene allowing infection by gibbon ape leukemia virus to human chromosome region 2q11-q14 and to the homologous region on mouse chromosome 2. *J. Virol*, in press (1991).

Kozak, M. Point mutations define a sequence flanking the AUG initiator codon that modulates translation by eukaryotic ribosomes. *Cell,* 44:283–292 (1986).

Kurtz, M. E.; Craff, R. J.; Adelman, A.; Martin-Morgan, D.; and Click, R. E. CTL and serologically defined antigens of the B2M, H-3 region. *J. Immunol* 135:2847–2852 (1985).

Kyte, J. and Doolittle, R. F. A simple method for displaying the hydropathic character of a protein. *Journal of Molecular Biology,* 157:105–132 (1982).

Maddon, P. J.; Dalgleish, A. G.; McDougal, J. S.; Clapham, P. R.; Weiss, R. A.; and Axel, R. The T4 gene encodes the AIDS virus receptor and is expressed in the immune system and the brain. *Cell,* 47:333–348 (1986).

McDougal, J. S.; Kennedy, M. S.; Sligh, J. M.; Cort, S. P.; Mawle, A.; and Nicholson, J. K. A. Binding of HTLV-III/LAV to T4+ cells by a complex of the 110K viral protein and the Tf molecule. *Science,* 231:382–385 (1986).

Mulligan, R. C. and Berg, P. *Proceedings of the National Academy of Sciences. USA,* 78:2072–2076 (1981).

Needleman, S. and Wunsch, C. J. A general method applicable to the search for similarity in the amino acid sequence in two proteins *Mol. Biol.,* 48:443–453 (1970).

Noda, T. M.; Satake, M.; Robins, T.; and Ito, Y. Isolation and characterization of NIH3T3 cells expressing polyoma small T antigen. *Journal of Virology,* 60:105–113 (1986).

O'Hara, B.; Johann, S. V.; Klinger, H. P.; Blair, D. G.; Rubinson, H.; Dunn, K. J.; Bass, P.; Vitek, S. M.; and Robins, T. Characterization of a human gene conferring sensitivity to infection by gibbon ape leukemia virus. *Cell Growth Differ.,* 3:119–127 (1990).

O'Hara, B.; Klinger, H. P.; Curran, T.; Zhang, Y.; and Blair, D. G. *Molecular and Cellular Biology,* 7:2941–2946 (1987).

Sanger, P.; Nicklen, 8.; and Coulson, A. R. DNA-sequencing with chain-terminating inhibitors. *Proc. Nationals Academy of Science. USA,* 74:5463–5467 (1977).

Southern, P. J. and Berg, P. *Journal of Molecular and Applied Genetics,* 1:327–351 (1982).

Vieira, J. and Messing, J. Production of single-stranded plasmid DNA. *Methods Enzymol.,* 153:3–11 (1987.

Weiss, R. N.; Teich, N.; Varmus, H.; Coffin, J. RNA Tumor Viruses: *Molecular Biology of Tumor Viruses,* Second Edition, Volume 1. Cold Spring Harbor Laboratories, Cold spring Harbor (1984).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3211 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GAGCTGTCCC  CGGTGCCGCC  GACCCGGGCC  GTGCCGTGTG  CCCGTGGCTC  CAGCCGCTGC      60

CGCCTCGATC  TCCTCGTCTC  CCGCTCCGCC  CTCCCTTTTC  CCTGGATGAA  CTTGCGTCCT     120

TTCTCTTCTC  CGCCATGGAA  TTCTGCTCCG  TGCTTTTAGC  CCTCCTGAGC  CAAAGAAACC     180

CCAGACAACA  GATGCCCATA  CGCAGCGTAT  AGCAGTAACT  CCCCAGCTCG  GTTTCTGTGC     240

CGTAGTTTAC  AGTATTTAAT  TTTATATAAT  ATATATTATT  TATTATAGCA  TTTTTGATAC     300

CTCATATTCT  GTTTACACAT  CTTGAAAGGC  GCTCAGTAGT  TCTCTTACTA  AACAACCACT     360

ACTCCAGAGA  ATGGCAACGC  TGATTACCAG  TACTACAGCT  GCTACCGCCG  CTTCTGGTCC     420

TTTGGTGGAC  TACCTATGGA  TGCTCATCCT  GGGCTTCATT  ATTGCATTTG  TCTTGGCATT     480

CTCCGTGGGA  GCCAATGATG  TAGCAAATTC  TTTTGGTACA  GCTGTGGGCT  CAGGTGTAGT     540

GACCCTGAAG  CAAGCCTGCA  TCCTAGCTAG  CATCTTTGAA  ACAGTGGGCT  CTGTCTTACT     600

GGGGGCCAAA  GTGAGCGAAA  CCATCCGGAA  GGGCTTGATT  GACGTGGAGA  TGTACAACTC     660
```

-continued

```
GACTCAAGGG CTACTGATGG CCGGCTCAGT CAGTGCTATG TTTGGTTCTG CTGTGTGGCA    720
ACTCGTGGCT TCGTTTTTGA AGCTCCCTAT TTCTGGAACC CATTGTATTG TTGGTGCAAC    780
TATTGGTTTC TCCCTCGTGG CAAAGGGGCA GGAGGGTGTC AAGTGGTCTG AACTGATAAA    840
AATTGTGATG TCTTGGTTCG TGTCCCCACT GCTTTCTGGA ATTATGTCTG GAATTTTATT    900
CTTCCTGGTT CGTGCATTCA TCCTCCATAA GGCAGATCCA GTTCCTAATG GTTTGCGAGC    960
TTTGCCAGTT TTCTATGCCT GCACAGTTGG AATAAACCTC TTTTCCATCA TGTATACTGG   1020
AGCACCGTTG CTGGGCTTTG ACAAACTTCC TCTGTGGGGT ACCATCCTCA TCTCGGTGGG   1080
ATGTGCAGTT TTCTGTGCCC TTATCGTCTG GTTCTTTGTA TGTCCCAGGA TGAAGAGAAA   1140
AATTGAACGA GAAATAAAGT GTAGTCCTTC TGAAAGCCCC TTAATGGAAA AAAAGAATAG   1200
CTTGAAAGAA GACCATGAAG AAACAAAGTT GTCTGTTGGT GATATTGAAA ACAACCATCC   1260
TGTTTCTGAG GTAGGGCCTG CCACTGTGCC CCTCCAGGCT GTGGTGGAGG AGAGAACAGT   1320
CTCATTCAAA CTTGGAGATT TGGAGGAAGC TCCAGAGAGA GAGAGGCTTC CCAGCGTGGA   1380
CTTGAAAGAG GAAACCAGCA TAGATAGCAC CGTGAATGGT GCAGTGCAGT TGCCTAATGG   1440
GAACCTTGTC CAGTTCACTC AAGCCGTCAG CAACCAAATA AACTCCAGTG CCACTCCCA    1500
GTATCACACC GTGCATAAGG ATTCCGGCCT GTACAAAGAG CTACTCCATA AATTACATCT   1560
TGCCAAGGTG GGAGATTGCA TGGGAGACTC CGGTGACAAA CCCTTAAGGC GCAATAATAG   1620
CTATACTTCC TATACCATGG CAATATGTGG CATGCCTCTG GATTCATTCC GTGCCAAAGA   1680
AGGTGAACAG AAGGGCGAAG AAATGGAGAA GCTGACATGG CCTAATGCAG ACTCCAAGAA   1740
GCGAATTCGA ATGGACAGTT ACACCAGTTA CTGCAATGCT GTGTCTGACC TTCACTCAGC   1800
ATCTGAGATA GACATGAGTG TCAAGGCAGC GATGGGTCTA GGTGACAGAA AAGGAAGTAA   1860
TGGCTCTCTA GAAGAATGGT ATGACCAGGA TAAGCCTGAA GTCTCTCTCC TCTTCCAGTT   1920
CCTGCAGATC CTTACAGCCT GCTTTGGGTC ATTCGCCCAT GGTGGCAATG ACGTAAGCAA   1980
TGCCATTGGG CCTCTGGTTG CTTTATATTT GGTTTATGAC ACAGGAGATG TTTCTTCAAA   2040
AGTGGCAACA CCAATATGGC TTCTACTCTA TGGTGGTGTT GGTATCTGTG TTGGTCTGTG   2100
GGTTTGGGGA AGAAGAGTTA TCCAGACCAT GGGGAAGGAT CTGACACCGA TCACACCCTC   2160
TAGTGGCTTC AGTATTGAAC TGGCATCTGC CCTCACTGTG GTGATTGCAT CAAATATTGG   2220
CCTTCCCATC AGTACAACAC ATTGTAAAGT GGGCTCTGTT GTGTCTGTTG CTGGCTCCG    2280
GTCCAAGAAG GCTGTTGACT GGCGTCTCTT TCGTAACATT TTTATGGCCT GGTTTGTCAC   2340
AGTCCCCATT TCTGGAGTTA TCAGTGCTGC CATCATGGCA ATCTTCAGAT ATGTCATCCT   2400
CAGAATGTGA AGCTGTTTGA GATTAAAATT TGTGTCAATG TTTGGGACCA TCTTAGGTAT   2460
TCCTGCTCCC CTGAAGAATG ATTACAGTGT TAACAGAAGA CTGACAAGAG TCTTTTTATT   2520
TGGGAGCAGA GGAGGGAAGT GTTACTTGTG CTATAACTGC TTTTGTGCTA AATATGAATT   2580
GTCTCAAAAT TAGCTGTGTA AAATAGCCCG GGTTCCACTG CTCCTGCTG AGGTCCCCTT    2640
TCCTTCTGGG CTGTGAATTC CTGTACATAT TTCTCTACTT TTTGTATCAG GCTTCAATTC   2700
CATTATGTTT TAATGTTGTC TCTGAAGATG ACTTGTGATT TTTTTTTCTT TTTTTAAAC    2760
CATGAAGAGC CGTTTGACAG AGCATGCTCT GCGTTGTTGG TTTCACCAGC TTCTGCCCTC   2820
ACATGCACAG GGATTTAACA ACAAAAATAT AACTACAACT TCCCTTGTAG TCTCTTATAT   2880
AAGTAGAGTC CTTGGTACTC TGCCCTCCTG TCAGTAGTGG CAGGATCTAT GGCATATTC    2940
GGGAGCTTCT TAGAGGGATG AGGTTCTTTG AACACAGTGA AAATTTAAAT TAGTAACTTT   3000
TTTGCAAGCA GTTTATTGAC TGTTATTGCT AAGAAGAAGT AAGAAAGAAA AAGCCTGTTG   3060
```

```
GCAATCTTGG  TTATTTCTTT  AAGATTTCTG  GCAGTGTGGG  ATGGATGAAT  GAAGTGGAAT      3120

GTGAACTTTG  GGCAAGTTAA  ATGGGACAGC  CTTCCATGTT  CATTTGTCTA  CCTCTTAACT      3180

GAATAAAAAA  GCCTACAGTT  TTTAGAAAAA  A                                      3211
```

( 2 ) INFORMATION FOR SEQ ID NO:2:

( i ) SEQUENCE CHARACTERISTICS:
        ( A ) LENGTH: 680 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ala Thr Leu Ile Thr Ser Thr Thr Ala Ala Thr Ala Ala Ser Gly
  1           5                  10                  15

Pro Leu Val Asp Tyr Leu Trp Met Leu Ile Leu Gly Phe Ile Ile Ala
             20                  25                  30

Phe Val Leu Ala Phe Ser Val Gly Ala Asn Asp Val Ala Asn Ser Phe
             35                  40                  45

Gly Thr Ala Val Gly Ser Gly Val Val Thr Leu Lys Gln Ala Cys Ile
 50                      55                  60

Leu Ala Ser Ile Phe Glu Thr Val Gly Ser Val Leu Leu Gly Ala Lys
 65                  70                      75                  80

Val Ser Glu Thr Ile Arg Lys Gly Leu Ile Asp Val Glu Met Tyr Asn
                 85                  90                  95

Ser Thr Gln Gly Leu Leu Met Ala Gly Ser Val Ser Ala Met Phe Gly
                100                 105                 110

Ser Ala Val Trp Gln Leu Val Ala Ser Phe Leu Lys Leu Pro Ile Ser
             115                 120                 125

Gly Thr His Cys Ile Val Gly Ala Thr Ile Gly Phe Ser Leu Val Ala
130                     135                 140

Lys Gly Gln Glu Gly Val Lys Trp Ser Glu Leu Ile Lys Ile Val Met
145                     150                 155                 160

Ser Trp Phe Val Ser Pro Leu Leu Ser Gly Ile Met Ser Gly Ile Leu
                 165                 170                 175

Phe Phe Leu Val Arg Ala Phe Ile Leu His Lys Ala Asp Pro Val Pro
             180                 185                 190

Asn Gly Leu Arg Ala Leu Pro Val Phe Tyr Ala Cys Thr Val Gly Ile
             195                 200                 205

Asn Leu Phe Ser Ile Met Tyr Thr Gly Ala Pro Leu Leu Gly Phe Asp
210                     215                 220

Lys Leu Pro Leu Trp Gly Thr Ile Leu Ile Ser Val Gly Cys Ala Val
225                     230                 235                 240

Phe Cys Ala Leu Ile Val Trp Phe Phe Val Cys Pro Arg Met Lys Arg
                 245                 250                 255

Lys Ile Glu Arg Glu Ile Lys Cys Ser Pro Ser Glu Ser Pro Leu Met
             260                 265                 270

Glu Lys Lys Asn Ser Leu Lys Glu Asp His Glu Glu Thr Lys Leu Ser
             275                 280                 285

Val Gly Asp Ile Glu Asn Lys His Pro Val Ser Glu Val Gly Pro Ala
290                     295                 300

Thr Val Pro Leu Gln Ala Val Val Glu Glu Arg Thr Val Ser Phe Lys
305                     310                 315                 320

Leu Gly Asp Leu Glu Glu Ala Pro Glu Arg Glu Arg Leu Pro Ser Val
```

|     |     |     |     |     | 325 |     |     |     | 330 |     |     |     | 335 |     |
| --- | --- | --- | --- | --- | --- | --- | --- | --- | --- | --- | --- | --- | --- | --- |
| Asp | Leu | Lys | Glu | Glu | Thr | Ser | Ile | Asp | Ser | Thr | Val | Asn | Gly | Ala | Val |
|     |     |     | 340 |     |     |     |     | 345 |     |     |     | 350 |     |     |
| Gln | Leu | Pro | Asn | Gly | Asn | Leu | Val | Gln | Phe | Ser | Gln | Ala | Val | Ser | Asn |
|     |     | 355 |     |     |     |     | 360 |     |     |     |     | 365 |     |     |
| Gln | Ile | Asn | Ser | Ser | Gly | His | Ser | Gln | Tyr | His | Thr | Val | His | Lys | Asp |
|     |     | 370 |     |     |     | 375 |     |     |     |     | 380 |     |     |     |
| Ser | Gly | Leu | Tyr | Lys | Glu | Leu | Leu | His | Lys | Leu | His | Leu | Ala | Lys | Val |
| 385 |     |     |     |     | 390 |     |     |     |     | 395 |     |     |     |     | 400 |
| Gly | Asp | Cys | Met | Gly | Asp | Ser | Gly | Asp | Lys | Pro | Leu | Arg | Arg | Asn | Asn |
|     |     |     |     | 405 |     |     |     |     | 410 |     |     |     |     | 415 |     |
| Ser | Tyr | Thr | Ser | Tyr | Thr | Met | Ala | Ile | Cys | Gly | Met | Pro | Leu | Asp | Ser |
|     |     |     | 420 |     |     |     |     | 425 |     |     |     |     | 430 |     |     |
| Phe | Arg | Ala | Lys | Glu | Gly | Glu | Gln | Lys | Gly | Glu | Glu | Met | Glu | Lys | Leu |
|     |     | 435 |     |     |     |     | 440 |     |     |     |     | 445 |     |     |     |
| Thr | Trp | Pro | Asn | Ala | Asp | Ser | Lys | Lys | Arg | Ile | Arg | Met | Asp | Ser | Tyr |
|     | 450 |     |     |     |     | 455 |     |     |     |     | 460 |     |     |     |     |
| Thr | Ser | Tyr | Cys | Asn | Ala | Val | Ser | Asp | Leu | His | Ser | Ala | Ser | Glu | Ile |
| 465 |     |     |     |     | 470 |     |     |     |     | 475 |     |     |     |     | 480 |
| Asp | Met | Ser | Val | Lys | Ala | Ala | Met | Gly | Leu | Gly | Asp | Arg | Lys | Gly | Ser |
|     |     |     |     | 485 |     |     |     |     | 490 |     |     |     |     | 495 |     |
| Asn | Gly | Ser | Leu | Glu | Glu | Trp | Tyr | Asp | Gln | Asp | Lys | Pro | Glu | Val | Ser |
|     |     |     | 500 |     |     |     |     | 505 |     |     |     |     | 510 |     |     |
| Leu | Leu | Phe | Gln | Phe | Leu | Gln | Ile | Leu | Thr | Ala | Cys | Phe | Gly | Ser | Phe |
|     |     | 515 |     |     |     |     | 520 |     |     |     |     | 525 |     |     |     |
| Ala | His | Gly | Gly | Asn | Asp | Val | Ser | Asn | Ala | Ile | Gly | Pro | Leu | Val | Ala |
|     | 530 |     |     |     |     | 535 |     |     |     |     | 540 |     |     |     |     |
| Leu | Tyr | Leu | Val | Tyr | Asp | Thr | Gly | Asp | Val | Ser | Ser | Lys | Val | Ala | Thr |
| 545 |     |     |     |     | 550 |     |     |     |     | 555 |     |     |     |     | 560 |
| Pro | Ile | Trp | Leu | Leu | Leu | Tyr | Gly | Gly | Val | Gly | Ile | Cys | Val | Gly | Leu |
|     |     |     |     | 565 |     |     |     |     | 570 |     |     |     |     | 575 |     |
| Trp | Val | Trp | Gly | Arg | Arg | Val | Ile | Gln | Thr | Met | Gly | Lys | Asp | Leu | Thr |
|     |     |     | 580 |     |     |     |     | 585 |     |     |     |     | 590 |     |     |
| Pro | Ile | Thr | Pro | Ser | Ser | Gly | Phe | Ser | Ile | Glu | Leu | Ala | Ser | Ala | Leu |
|     |     | 595 |     |     |     |     | 600 |     |     |     |     | 605 |     |     |     |
| Thr | Val | Val | Ile | Ala | Ser | Asn | Ile | Gly | Leu | Pro | Ile | Ser | Thr | Thr | His |
|     | 610 |     |     |     |     | 615 |     |     |     |     | 620 |     |     |     |     |
| Cys | Lys | Val | Gly | Ser | Val | Ser | Val | Ser | Val | Gly | Trp | Leu | Arg | Ser | Lys |
| 625 |     |     |     |     | 630 |     |     |     |     | 635 |     |     |     |     | 640 |
| Ala | Val | Asp | Trp | Arg | Leu | Phe | Arg | Asn | Ile | Phe | Met | Ala | Trp | Phe | Val |
|     |     |     |     | 645 |     |     |     |     | 650 |     |     |     |     | 655 |     |
| Thr | Val | Pro | Ile | Ser | Gly | Val | Ile | Ser | Ala | Ala | Ile | Met | Ala | Ile | Phe |
|     |     |     | 660 |     |     |     |     | 665 |     |     |     |     | 670 |     |     |
| Arg | Tyr | Val | Ile | Leu | Arg | Met | Xaa |
|     |     | 675 |     |     |     |     | 680 |

( 2 ) INFORMATION FOR SEQ ID NO:3:

( i ) SEQUENCE CHARACTERISTICS:
        ( A ) LENGTH: 3260 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

(A) NAME/KEY: CDS
(B) LOCATION: 443..2488

(xi) SEQUENCE DESCRIPTION: SEQ ID NO:3:

| | | | | |
|---|---|---|---|---|
| GACGGTATCG | ATAAGCTTGA | TATCGAATTC | CCTGTGCTCC | ACCTTGCACA | GCGTTTGGGG | 60 |
| GACTGAAGAC | ATAAGTGACG | GGCGGGGGGG | GGGGGGACTA | TGCGGAGTCC | CAGGCTGCCC | 120 |
| TCTTCCAGA | GATGCGCCGC | TATTGTTATT | TTCTTCCACT | TCGTCCCCCC | AGGATGAACT | 180 |
| TGCGTCCTTT | CTCTAATCCG | CCATGGAATT | CTGCTCCGTG | CTTTTAGCCC | TCCAGAGCCA | 240 |
| AAGAAACCCC | AGACAACAGA | CGCCCAGACG | CAGCAGCGTA | TAGCAGTAAC | TCCCCAGCTC | 300 |
| GGTTTCCGTG | CCGTAGTTTA | CAGTATTTAA | TTTTATATAA | TATATACTAT | TTATTATAGC | 360 |
| ATTTTGATAC | CTCATTCCGT | TTACACATCT | CAAAAGCCGC | TTAGTAATTC | TCTTATTATT | 420 |
| TAAAGAACCA | CTACACTAGA | GA ATG GAA | TCT ACT GTG | GCA ACG ATT | ACT AGT | 472 |

```
                           Met Glu Ser Thr Val Ala Thr Ile Thr Ser
                             1               5                  10

ACC CTA GCT GCT GTT ACT GCT TCC GCT CCA CCG AAG TAT GAC AAT CTA       520
Thr Leu Ala Ala Val Thr Ala Ser Ala Pro Pro Lys Tyr Asp Asn Leu
            15                  20                  25

TGG ATG CTC ATC CTG GGC TTC ATC ATT GCA TTT GTC TTG GCA TTC TCC       568
Trp Met Leu Ile Leu Gly Phe Ile Ile Ala Phe Val Leu Ala Phe Ser
        30                      35                  40

GTG GGA GCC AAT GAT GTA GCA AAT TCG TTC GGT ACA GCT GTA GGC TCA       616
Val Gly Ala Asn Asp Val Ala Asn Ser Phe Gly Thr Ala Val Gly Ser
    45                      50                  55

GGT GTA GTG ACC CTG AAG CAA GCC TGC ATC TTA GCT AGC ATC TTC GAA       664
Gly Val Val Thr Leu Lys Gln Ala Cys Ile Leu Ala Ser Ile Phe Glu
        60                  65                      70

ACT GTG GGC TCC GCC TTG CTG GGG GCC AAA GTG AGC GAA ACC ATC CGG       712
Thr Val Gly Ser Ala Leu Leu Gly Ala Lys Val Ser Glu Thr Ile Arg
75                  80                  85                      90

AAC GGC TTG ATA GAT GTG GAG CTG TAC AAC GAA ACT CAA GAT CTG CTC       760
Asn Gly Leu Ile Asp Val Glu Leu Tyr Asn Glu Thr Gln Asp Leu Leu
            95                      100                 105

ATG GCT GGC TCC GTC AGT GCT ATG TTT GGT TCT GCT GTG TGG CAG CTC       808
Met Ala Gly Ser Val Ser Ala Met Phe Gly Ser Ala Val Trp Gln Leu
            110                     115                 120

GTG GCT TCG TTT TTG AAG CTT CCG ATT TCT GGG ACC CAT TGT ATT GTC       856
Val Ala Ser Phe Leu Lys Leu Pro Ile Ser Gly Thr His Cys Ile Val
        125                     130                 135

GGT GCA ACC ATT GGT TTC TCC CTT GTG GCA AAT GGG CAG AAG GGT GTC       904
Gly Ala Thr Ile Gly Phe Ser Leu Val Ala Asn Gly Gln Lys Gly Val
        140                     145                 150

AAG TGG TCT GAA CTG ATA AAA ATT GTG ATG TCG TGG TTC GTC TCT CCG       952
Lys Trp Ser Glu Leu Ile Lys Ile Val Met Ser Trp Phe Val Ser Pro
155                 160                 165                     170

CTG CTT TCT GGT ATT ATG TCT GGA ATT TTA TTC TTC CTT GTT CGT GCG       1000
Leu Leu Ser Gly Ile Met Ser Gly Ile Leu Phe Phe Leu Val Arg Ala
                175                     180                 185

TTC ATC CTC CGT AAG GCA GAT CCG GTT CCT AAT GGC TTA CGA GCT TTA       1048
Phe Ile Leu Arg Lys Ala Asp Pro Val Pro Asn Gly Leu Arg Ala Leu
            190                     195                 200

CCA ATT TTT TAT GCC TGC ACA ATC GGA ATC AAC CTC TTT TCC ATT ATG       1096
Pro Ile Phe Tyr Ala Cys Thr Ile Gly Ile Asn Leu Phe Ser Ile Met
            205                     210                 215

TAT ACT GGA GCA CCG TTG CTG GGC TTT GAC AAA CTT CCT CTG TGG GGT       1144
Tyr Thr Gly Ala Pro Leu Leu Gly Phe Asp Lys Leu Pro Leu Trp Gly
            220                 225                     230

ACC ATC CTC ATC TCG GTG GGA TGT GCA GTT TTC TGT GCC CTT ATC GTC       1192
```

| | | | | | | | | | | | | | | | | |
|---|---|---|---|---|---|---|---|---|---|---|---|---|---|---|---|---|
| Thr<br>235 | Ile | Leu | Ile | Ser | Val<br>240 | Gly | Cys | Ala | Val<br>245 | Phe | Cys | Ala | Leu | Ile<br>250 | Val | |
| TGG<br>Trp | TTC<br>Phe | TTT<br>Phe | GTA<br>Val | TGT<br>Cys<br>255 | CCC<br>Pro | AGG<br>Arg | ATG<br>Met | AAG<br>Lys | AGA<br>Arg<br>260 | AAA<br>Lys | ATT<br>Ile | GAA<br>Glu | CGA<br>Arg | GAA<br>Glu<br>265 | GTA<br>Val | 1240 |
| AAG<br>Lys | TCT<br>Ser | AGT<br>Ser | CCG<br>Pro<br>270 | TCT<br>Ser | GAA<br>Glu | AGT<br>Ser | CCC<br>Pro | TTA<br>Leu<br>275 | ATG<br>Met | GAA<br>Glu | AAG<br>Lys | AAG<br>Lys | AGC<br>Ser<br>280 | AAC<br>Asn | TTA<br>Leu | 1288 |
| AAA<br>Lys | GAA<br>Glu | GAC<br>Asp | CAT<br>His<br>285 | GAA<br>Glu | GAA<br>Glu | ACA<br>Thr | AAG<br>Lys | ATG<br>Met<br>290 | GCT<br>Ala | CCT<br>Pro | GGA<br>Gly | GAC<br>Asp | GTT<br>Val<br>295 | GAG<br>Glu | CAT<br>His | 1336 |
| AGG<br>Arg | AAT<br>Asn<br>300 | CCT<br>Pro | GTG<br>Val | TCT<br>Ser | GAG<br>Glu | GTA<br>Val<br>305 | GTG<br>Val | TGT<br>Cys | GCC<br>Ala | ACT<br>Thr | GGG<br>Gly<br>310 | CCA<br>Pro | CTC<br>Leu | CGG<br>Arg | GCT<br>Ala | 1384 |
| GTG<br>Val<br>315 | GTG<br>Val | GAG<br>Glu | GAG<br>Glu | AGG<br>Arg | ACG<br>Thr<br>320 | GTG<br>Val | TCA<br>Ser | TTC<br>Phe | AAA<br>Lys | CTT<br>Leu<br>325 | GGT<br>Gly | GAC<br>Asp | CTG<br>Leu | GAG<br>Glu | GAG<br>Glu<br>330 | 1432 |
| GCT<br>Ala | CCG<br>Pro | GAG<br>Glu | CGA<br>Arg | GAG<br>Glu<br>335 | CGG<br>Arg | CTT<br>Leu | CCC<br>Pro | ATG<br>Met | GAC<br>Asp<br>340 | CTG<br>Leu | AAG<br>Lys | GAG<br>Glu | GAG<br>Glu | ACC<br>Thr<br>345 | AGC<br>Ser | 1480 |
| ATA<br>Ile | GAC<br>Asp | AGC<br>Ser | ACC<br>Thr<br>350 | ATC<br>Ile | AAT<br>Asn | GGT<br>Gly | GCA<br>Ala | GTG<br>Val<br>355 | CAG<br>Gln | TTG<br>Leu | CCT<br>Pro | AAT<br>Asn | GGG<br>Gly<br>360 | AAC<br>Asn | CTT<br>Leu | 1528 |
| GTT<br>Val | CAG<br>Gln | TTC<br>Phe<br>365 | AGT<br>Ser | CAA<br>Gln | ACT<br>Thr | GTC<br>Val | AGC<br>Ser<br>370 | AAC<br>Asn | CAG<br>Gln | ATC<br>Ile | AAC<br>Asn | TCC<br>Ser<br>375 | AGT<br>Ser | GGC<br>Gly | CAC<br>His | 1576 |
| TAT<br>Tyr | CAG<br>Gln | TAT<br>Tyr<br>380 | CAC<br>His | ACC<br>Thr | GTG<br>Val | CAC<br>His | AAG<br>Lys<br>385 | GAT<br>Asp | TCT<br>Ser | GGC<br>Gly | TTG<br>Leu | TAC<br>Tyr<br>390 | AAG<br>Lys | GAG<br>Glu | CTG<br>Leu | 1624 |
| CTC<br>Leu<br>395 | CAT<br>His | AAG<br>Lys | TTA<br>Leu | CAT<br>His | CTG<br>Leu<br>400 | GCC<br>Ala | AAG<br>Lys | GTG<br>Val | GGA<br>Gly | GAC<br>Asp<br>405 | TGC<br>Cys | ATG<br>Met | GGA<br>Gly | GAT<br>Asp | TCT<br>Ser<br>410 | 1672 |
| GGG<br>Gly | GAC<br>Asp | AAG<br>Lys | CCC<br>Pro | TTG<br>Leu<br>415 | AGA<br>Arg | CGC<br>Arg | AAC<br>Asn | AAC<br>Asn | AGC<br>Ser<br>420 | TAC<br>Tyr | ACT<br>Thr | TCC<br>Ser | TAC<br>Tyr | ACT<br>Thr<br>425 | ATG<br>Met | 1720 |
| GCA<br>Ala | ATA<br>Ile | TGT<br>Cys | GGC<br>Gly<br>430 | ATG<br>Met | CCC<br>Pro | CTG<br>Leu | GAT<br>Asp | TCA<br>Ser<br>435 | TTC<br>Phe | CGT<br>Arg | GCC<br>Ala | AAA<br>Lys | GAA<br>Glu<br>440 | GGT<br>Gly | GAA<br>Glu | 1768 |
| CAA<br>Gln | AAG<br>Lys | GGA<br>Gly<br>445 | GAT<br>Asp | GAA<br>Glu | ATG<br>Met | GAG<br>Glu | ACG<br>Thr<br>450 | CTG<br>Leu | ACA<br>Thr | TGG<br>Trp | CCT<br>Pro | AAT<br>Asn<br>455 | GCA<br>Ala | GAT<br>Asp | ACC<br>Thr | 1816 |
| AAG<br>Lys | AAG<br>Lys<br>460 | CGG<br>Arg | ATT<br>Ile | CGA<br>Arg | ATG<br>Met<br>465 | GAC<br>Asp | AGT<br>Ser | TAC<br>Tyr | ACC<br>Thr | AGT<br>Ser<br>470 | TAC<br>Tyr | TGC<br>Cys | AAT<br>Asn | GCC<br>Ala | GTG<br>Val | 1864 |
| TCT<br>Ser<br>475 | GAC<br>Asp | CTT<br>Leu | CAC<br>His | TCC<br>Ser | GAG<br>Glu<br>480 | TCT<br>Ser | GAG<br>Glu | ATG<br>Met | GAC<br>Asp | ATG<br>Met<br>485 | AGT<br>Ser | GTG<br>Val | AAG<br>Lys | GCT<br>Ala | GAG<br>Glu<br>490 | 1912 |
| ATG<br>Met | GGC<br>Gly | CTG<br>Leu | GGT<br>Gly | GAC<br>Asp<br>495 | AGA<br>Arg | AAA<br>Lys | GGA<br>Gly | AGC<br>Ser | AGT<br>Ser<br>500 | GGC<br>Gly | TCT<br>Ser | CTT<br>Leu | GAA<br>Glu | GAA<br>Glu<br>505 | TGG<br>Trp | 1960 |
| TAT<br>Tyr | GAC<br>Asp | CAG<br>Gln | GAT<br>Asp<br>510 | AAG<br>Lys | CCT<br>Pro | GAA<br>Glu | GTG<br>Val | TCC<br>Ser<br>515 | CTT<br>Leu | CTC<br>Leu | TTC<br>Phe | CAG<br>Gln | TTC<br>Phe<br>520 | CTG<br>Leu | CAG<br>Gln | 2008 |
| ATC<br>Ile | CTT<br>Leu | ACA<br>Thr<br>525 | GCC<br>Ala | TGC<br>Cys | TTT<br>Phe | GGG<br>Gly | TCA<br>Ser<br>530 | TTT<br>Phe | GCC<br>Ala | CAT<br>His | GGT<br>Gly | GGC<br>Gly<br>535 | AAT<br>Asn | GAC<br>Asp | GTC<br>Val | 2056 |
| AGC<br>Ser | AAT<br>Asn<br>540 | GCC<br>Ala | ATC<br>Ile | GGC<br>Gly | CCT<br>Pro<br>545 | CTG<br>Leu | GTT<br>Val | GCT<br>Ala | TTG<br>Leu | TAT<br>Tyr<br>550 | CTT<br>Leu | GTT<br>Val | TAT<br>Tyr | AAA<br>Lys | CAA<br>Gln | 2104 |
| GAA | GCC | TCT | ACA | AAA | GCG | GCA | ACA | CCC | ATA | TGG | CTT | CTG | CTT | TAT | GGT | 2152 |

| | | | | | | | | | | | | | | | |
|---|---|---|---|---|---|---|---|---|---|---|---|---|---|---|---|
| Glu | Ala | Ser | Thr | Lys | Ala | Ala | Thr | Pro | Ile | Trp | Leu | Leu | Leu | Tyr | Gly |
| 555 | | | | 560 | | | | | 565 | | | | | | 570 |

| GGT | GTT | GGC | ATT | TGC | ATG | GGC | CTG | TGG | GTT | TGG | GGA | AGA | AGA | GTT | ATC | 2200 |
|---|---|---|---|---|---|---|---|---|---|---|---|---|---|---|---|---|
| Gly | Val | Gly | Ile | Cys | Met | Gly | Leu | Trp | Val | Trp | Gly | Arg | Arg | Val | Ile | |
| | | | | 575 | | | | 580 | | | | | 585 | | | |

| CAG | ACC | ATG | GGG | AAG | GAC | CTG | ACC | CCA | ATC | ACA | CCC | TCC | AGT | GGT | TTC | 2248 |
|---|---|---|---|---|---|---|---|---|---|---|---|---|---|---|---|---|
| Gln | Thr | Met | Gly | Lys | Asp | Leu | Thr | Pro | Ile | Thr | Pro | Ser | Ser | Gly | Phe | |
| | | | 590 | | | | | 595 | | | | | 600 | | | |

| AGT | ATT | GAA | CTG | GCG | TCT | GCC | TTA | ACT | GTG | GTC | ATC | GCA | TCA | AAC | ATT | 2296 |
|---|---|---|---|---|---|---|---|---|---|---|---|---|---|---|---|---|
| Ser | Ile | Glu | Leu | Ala | Ser | Ala | Leu | Thr | Val | Val | Ile | Ala | Ser | Asn | Ile | |
| | | 605 | | | | | 610 | | | | 615 | | | | | |

| GGC | CTT | CCC | ATC | AGC | ACA | ACA | CAT | TGC | AAA | GTG | GGC | TCT | GTT | GTG | TCT | 2344 |
|---|---|---|---|---|---|---|---|---|---|---|---|---|---|---|---|---|
| Gly | Leu | Pro | Ile | Ser | Thr | Thr | His | Cys | Lys | Val | Gly | Ser | Val | Val | Ser | |
| | 620 | | | | | 625 | | | | | 630 | | | | | |

| GTT | GGC | TGG | CTC | CGA | TCA | AAG | AAG | GCT | GTT | GAC | TGG | CGA | CTG | TTT | CGA | 2392 |
|---|---|---|---|---|---|---|---|---|---|---|---|---|---|---|---|---|
| Val | Gly | Trp | Leu | Arg | Ser | Lys | Lys | Ala | Val | Asp | Trp | Arg | Leu | Phe | Arg | |
| 635 | | | | | 640 | | | | | 645 | | | | | 650 | |

| AAC | ATT | TTT | ATG | GCC | TGG | TTT | GTC | ACG | GTC | CCC | ATC | TCT | GGG | GTT | ATC | 2440 |
|---|---|---|---|---|---|---|---|---|---|---|---|---|---|---|---|---|
| Asn | Ile | Phe | Met | Ala | Trp | Phe | Val | Thr | Val | Pro | Ile | Ser | Gly | Val | Ile | |
| | | | | 655 | | | | | 660 | | | | | 665 | | |

| AGT | GCC | GCT | ATC | ATG | GCA | GTA | TTC | AAG | TAC | ATC | ATC | CTG | CCA | GTG | TGA | 2488 |
|---|---|---|---|---|---|---|---|---|---|---|---|---|---|---|---|---|
| Ser | Ala | Ala | Ile | Met | Ala | Val | Phe | Lys | Tyr | Ile | Ile | Leu | Pro | Val | Xaa | |
| | | | 670 | | | | | 675 | | | | | 680 | | | |

| CGCTGGGGTT | GAAAGCTGTG | TCAGTGTCTG | GGACCATTGT | ACACATTCCT | GTTCCTAGGA | 2548 |
|---|---|---|---|---|---|---|
| GAACGCTCAC | AGTGTGGCTG | AAGACAGGCA | AGGGTCTTAA | AGGAGCCGTG | GGAAGGAAGT | 2608 |
| GTAATTTACA | CTATAATTGC | TTTTGTGCTA | AATATGACTT | ATCTCAAAAT | TAGCTATGTA | 2668 |
| AAATAGCCAG | GTTTCCATTG | ATTCATTCCA | AGGTCCCTTT | TCTCCTGGGC | TATGAATTCC | 2728 |
| TGTACATATT | TCTCTACTTT | TGTATCAGGC | CTCAATTCCA | GTATGTTTTA | ATGTTGTCTG | 2788 |
| TGAGATAACT | TAGGTGGGTT | CTTTTAAAC | AGCCAGCAGA | GCCATTTGAT | GGCATGTACT | 2848 |
| GCTTTGTCGG | CCTCACCAGC | TTCTTCCCCA | ACATGCACAG | GGATTTAACA | ACATGTAACT | 2908 |
| GAAGCTTCCC | TCCCTCATAG | TCTCTCATAG | AAATAGTCAC | GGCACTCTGC | TCCCTGTCAC | 2968 |
| TAGTGGCAGG | TTCTGTTGAT | GTGTGACAAC | TTCTTAGAGG | GCCGAGAATC | TTTGGCACAG | 3028 |
| TGGAAATATA | AGTTTGTAGT | AACCTCTTTG | CAAACAGTTC | ACGGACATGT | TGCTAAGAAG | 3088 |
| CAGGGAGACA | AAGCCCCTGG | CGGTTGTGGT | TATTCTTCTG | AGATTTCTGG | CAGTGTGGGA | 3148 |
| TGGGTGAATG | AAGTGGAATG | TGAACTTTGG | GCAAATTCAA | TGGGACAGCC | TTCCATGTTC | 3208 |
| ATCTGTCTAC | CTCTTAACTG | AATAAAAAGC | CTACAGTTTT | TAAAAAAAAA | AA | 3260 |

( 2 ) INFORMATION FOR SEQ ID NO:4:

( i ) SEQUENCE CHARACTERISTICS:
        ( A ) LENGTH: 682 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Ser | Thr | Val | Ala | Thr | Ile | Thr | Ser | Thr | Leu | Ala | Ala | Val | Thr |
|---|---|---|---|---|---|---|---|---|---|---|---|---|---|---|---|
| 1 | | | | 5 | | | | | 10 | | | | | 15 | |

| Ala | Ser | Ala | Pro | Pro | Lys | Tyr | Asp | Asn | Leu | Trp | Met | Leu | Ile | Leu | Gly |
|---|---|---|---|---|---|---|---|---|---|---|---|---|---|---|---|
| | | | 20 | | | | | 25 | | | | | 30 | | |

| Phe | Ile | Ile | Ala | Phe | Val | Leu | Ala | Phe | Ser | Val | Gly | Ala | Asn | Asp | Val |
|---|---|---|---|---|---|---|---|---|---|---|---|---|---|---|---|
| | | | 35 | | | | 40 | | | | | 45 | | | |

| Ala | Asn | Ser | Phe | Gly | Thr | Ala | Val | Gly | Ser | Gly | Val | Val | Thr | Leu | Lys |
|---|---|---|---|---|---|---|---|---|---|---|---|---|---|---|---|
| | 50 | | | | | 55 | | | | | 60 | | | | |

```
Gln Ala Cys Ile Leu Ala Ser Ile Phe Glu Thr Val Gly Ser Ala Leu
 65                  70                  75                  80

Leu Gly Ala Lys Val Ser Glu Thr Ile Arg Asn Gly Leu Ile Asp Val
                 85                  90                  95

Glu Leu Tyr Asn Glu Thr Gln Asp Leu Leu Met Ala Gly Ser Val Ser
            100                 105                 110

Ala Met Phe Gly Ser Ala Val Trp Gln Leu Val Ala Ser Phe Leu Lys
        115                 120                 125

Leu Pro Ile Ser Gly Thr His Cys Ile Val Gly Ala Thr Ile Gly Phe
130                 135                 140

Ser Leu Val Ala Asn Gly Gln Lys Gly Val Lys Trp Ser Glu Leu Ile
145                 150                 155                 160

Lys Ile Val Met Ser Trp Phe Val Ser Pro Leu Leu Ser Gly Ile Met
                165                 170                 175

Ser Gly Ile Leu Phe Phe Leu Val Arg Ala Phe Ile Leu Arg Lys Ala
            180                 185                 190

Asp Pro Val Pro Asn Gly Leu Arg Ala Leu Pro Ile Phe Tyr Ala Cys
        195                 200                 205

Thr Ile Gly Ile Asn Leu Phe Ser Ile Met Tyr Thr Gly Ala Pro Leu
210                 215                 220

Leu Gly Phe Asp Lys Leu Pro Leu Trp Gly Thr Ile Leu Ile Ser Val
225                 230                 235                 240

Gly Cys Ala Val Phe Cys Ala Leu Ile Val Trp Phe Phe Val Cys Pro
                245                 250                 255

Arg Met Lys Arg Lys Ile Glu Arg Glu Val Lys Ser Ser Pro Ser Glu
            260                 265                 270

Ser Pro Leu Met Glu Lys Lys Ser Asn Leu Lys Glu Asp His Glu Glu
        275                 280                 285

Thr Lys Met Ala Pro Gly Asp Val Glu His Arg Asn Pro Val Ser Glu
290                 295                 300

Val Val Cys Ala Thr Gly Pro Leu Arg Ala Val Val Glu Glu Arg Thr
305                 310                 315                 320

Val Ser Phe Lys Leu Gly Asp Leu Glu Glu Ala Pro Glu Arg Glu Arg
                325                 330                 335

Leu Pro Met Asp Leu Lys Glu Glu Thr Ser Ile Asp Ser Thr Ile Asn
            340                 345                 350

Gly Ala Val Gln Leu Pro Asn Gly Asn Leu Val Gln Phe Ser Gln Thr
        355                 360                 365

Val Ser Asn Gln Ile Asn Ser Ser Gly His Tyr Gln Tyr His Thr Val
370                 375                 380

His Lys Asp Ser Gly Leu Tyr Lys Glu Leu Leu His Lys Leu His Leu
385                 390                 395                 400

Ala Lys Val Gly Asp Cys Met Gly Asp Ser Gly Asp Lys Pro Leu Arg
                405                 410                 415

Arg Asn Asn Ser Tyr Thr Ser Tyr Thr Met Ala Ile Cys Gly Met Pro
            420                 425                 430

Leu Asp Ser Phe Arg Ala Lys Glu Gly Glu Gln Lys Gly Asp Glu Met
        435                 440                 445

Glu Thr Leu Thr Trp Pro Asn Ala Asp Thr Lys Lys Arg Ile Arg Met
450                 455                 460

Asp Ser Tyr Thr Ser Tyr Cys Asn Ala Val Ser Asp Leu His Ser Glu
465                 470                 475                 480

Ser Glu Met Asp Met Ser Val Lys Ala Glu Met Gly Leu Gly Asp Arg
```

|   |   |   |   |   |   |   |   |   |   |   |   |   |   |   |   |
|---|---|---|---|---|---|---|---|---|---|---|---|---|---|---|---|
|   |   |   |   | 485 |   |   |   |   | 490 |   |   |   |   | 495 |   |
| Lys | Gly | Ser | Ser<br>500 | Gly | Ser | Leu | Glu | Glu<br>505 | Trp | Tyr | Asp | Gln | Asp<br>510 | Lys | Pro |
| Glu | Val | Ser<br>515 | Leu | Leu | Phe | Gln | Phe<br>520 | Leu | Gln | Ile | Leu | Thr<br>525 | Ala | Cys | Phe |
| Gly | Ser<br>530 | Phe | Ala | His | Gly | Gly<br>535 | Asn | Asp | Val | Ser | Asn<br>540 | Ala | Ile | Gly | Pro |
| Leu<br>545 | Val | Ala | Leu | Tyr | Leu<br>550 | Val | Tyr | Lys | Gln | Glu<br>555 | Ala | Ser | Thr | Lys | Ala<br>560 |
| Ala | Thr | Pro | Ile | Trp<br>565 | Leu | Leu | Leu | Tyr | Gly<br>570 | Gly | Val | Gly | Ile | Cys<br>575 | Met |
| Gly | Leu | Trp | Val<br>580 | Trp | Gly | Arg | Arg | Val<br>585 | Ile | Gln | Thr | Met | Gly<br>590 | Lys | Asp |
| Leu | Thr | Pro<br>595 | Ile | Thr | Pro | Ser | Ser<br>600 | Gly | Phe | Ser | Ile | Glu<br>605 | Leu | Ala | Ser |
| Ala | Leu<br>610 | Thr | Val | Val | Ile | Ala<br>615 | Ser | Asn | Ile | Gly | Leu<br>620 | Pro | Ile | Ser | Thr |
| Thr<br>625 | His | Cys | Lys | Val | Gly<br>630 | Ser | Val | Val | Ser | Val<br>635 | Gly | Trp | Leu | Arg | Ser<br>640 |
| Lys | Lys | Ala | Val | Asp<br>645 | Trp | Arg | Leu | Phe | Arg<br>650 | Asn | Ile | Phe | Met | Ala<br>655 | Trp |
| Phe | Val | Thr | Val<br>660 | Pro | Ile | Ser | Gly | Val<br>665 | Ile | Ser | Ala | Ala | Ile<br>670 | Met | Ala |
| Val | Phe | Lys<br>675 | Tyr | Ile | Ile | Leu | Pro<br>680 | Val | Xaa |   |   |   |   |   |   |

What is claimed is:

1. A recombinant gibbon ape leukemia virus receptor protein having the amino acid sequence selected from the group consisting of SEQ ID NO: 2 and SEQ ID NO: 4.

2. A plasmid which contains a nucleotide sequence encoding a human gibbon ape leukemia virus receptor with an SV40 early promoter upstream and an SV40 polyadenylation signal downstream deposited under ATCC Accession Number 68070.

3. A plasmid which contains a nucleotide sequence encoding a murine gibbon ape leukemia virus receptor deposited under ATCC Accession Number 68517.

4. A method for identifying DNA encoding gibbon ape leukemia virus receptor protein homologs comprising the steps of:

(a) selecting a DNA probe having a nucleotide sequence selected from the group consisting of SEQ ID NO: 1, SEQ ID NO: 3, and fragments thereof; and (b) isolating DNA encoding a gibbon ape leukemia virus receptor protein with the DNA probe of step (a).

* * * * *